United States Patent
Jehan

(10) Patent No.: US 10,282,163 B2
(45) Date of Patent: May 7, 2019

(54) CADENCE AND MEDIA CONTENT PHASE ALIGNMENT

(71) Applicant: Spotify AB, Stockholm (SE)

(72) Inventor: Tristan Jehan, Brooklyn, NY (US)

(73) Assignee: SPOTIFY AB, Stockholm (SE)

( * ) Notice: Subject to any disclaimer, the term of this patent is extended or adjusted under 35 U.S.C. 154(b) by 106 days.

(21) Appl. No.: 15/396,253

(22) Filed: Dec. 30, 2016

(65) Prior Publication Data

US 2017/0177297 A1    Jun. 22, 2017

Related U.S. Application Data

(63) Continuation of application No. 14/883,318, filed on Oct. 14, 2015, now Pat. No. 9,568,994.
(Continued)

(51) Int. Cl.
*G06F 17/00* (2006.01)
*G06F 3/16* (2006.01)
(Continued)

(52) U.S. Cl.
CPC .............. *G06F 3/165* (2013.01); *A61B 5/024* (2013.01); *A63B 71/00* (2013.01);
(Continued)

(58) Field of Classification Search
CPC ............ A61B 5/024; A63B 2071/0625; A63B 2230/06; A63B 71/00; A63B 71/0622;
(Continued)

(56) References Cited

U.S. PATENT DOCUMENTS

| 7,767,897 B2 | 8/2010 | Jochelson et al. |
| 8,738,925 B1 | 5/2014 | Park et al. |

(Continued)

FOREIGN PATENT DOCUMENTS

| EP | 1 705 588 A1 | 9/2006 |
| WO | 2014/109982 A2 | 7/2014 |

OTHER PUBLICATIONS

U.S. Appl. No. 14/883,340, filed Oct. 14, 2015 for "Cadence-Based Selection, Playback, and Transition Between Song Versions".
(Continued)

*Primary Examiner* — Paul C McCord
(74) *Attorney, Agent, or Firm* — Merchant & Gould P.C.

(57) ABSTRACT

Systems, devices, apparatuses, components, methods, and techniques for cadence and media content phase alignment are provided. An example media-playback device includes a content output device that operates to output media content, a cadence-acquiring device, a phase-delay calibration engine, a cadence-based media content selection engine, and a phase-aligned media playback engine. The cadence-acquiring device includes a movement-determining device and a cadence-determination engine configured to determine a cadence based on movement data captured by the movement-determining device. The phase-delay calibration engine configured to determine phase delay values for at least one cadence value. The cadence-based media content selection engine configured to identify a media content item based on the cadence determined by the cadence-acquiring device. The phase-aligned media playback engine configured to align the identified media content item to the repetitive-motion activity and cause the media-output device to output the aligned media content item.

20 Claims, 13 Drawing Sheets

Related U.S. Application Data

(60) Provisional application No. 62/163,856, filed on May 19, 2015.

(51) Int. Cl.
    *G06F 17/30* (2006.01)
    *A61B 5/024* (2006.01)
    *A63B 71/00* (2006.01)
    *G06F 3/01* (2006.01)
    *A63B 71/06* (2006.01)

(52) U.S. Cl.
    CPC .......... *A63B 71/0622* (2013.01); *G06F 3/011* (2013.01); *G06F 17/30755* (2013.01); *G06F 17/30764* (2013.01); *A63B 2071/0625* (2013.01); *A63B 2230/062* (2013.01)

(58) Field of Classification Search
    CPC ......... G06F 17/30755; G06F 17/30764; G06F 3/011; G06F 3/165
    USPC .......................................... 700/94
    See application file for complete search history.

(56) References Cited

U.S. PATENT DOCUMENTS

| | | |
|---|---|---|
| 8,932,218 B1 | 1/2015 | Thompson |
| 2002/0093841 A1 | 7/2002 | Kitayama et al. |
| 2002/0107649 A1 | 8/2002 | Takiguchi et al. |
| 2002/0172379 A1 | 11/2002 | Cliff |
| 2004/0122662 A1 | 6/2004 | Crockett |
| 2005/0286213 A1 | 12/2005 | Rooney |
| 2006/0000344 A1 | 1/2006 | Basu |
| 2006/0107822 A1 | 5/2006 | Bowen |
| 2006/0253210 A1 | 11/2006 | Rosenberg |
| 2007/0137464 A1 | 6/2007 | Moulios et al. |
| 2007/0240558 A1 | 10/2007 | Seppanen et al. |
| 2007/0254271 A1 | 11/2007 | Burlik et al. |
| 2007/0261537 A1 | 11/2007 | Eronen et al. |
| 2008/0096726 A1 | 4/2008 | Riley et al. |
| 2008/0097633 A1 | 4/2008 | Jochelson et al. |
| 2008/0153671 A1 | 6/2008 | Ogg et al. |
| 2008/0314232 A1 | 12/2008 | Hansson et al. |
| 2009/0319221 A1 | 12/2009 | Kahn et al. |
| 2010/0030085 A1 | 2/2010 | Rojas Ojeda et al. |
| 2011/0153042 A1 | 6/2011 | Burton et al. |
| 2012/0059494 A1 | 3/2012 | David |
| 2012/0136573 A1 | 5/2012 | Janardhanan et al. |
| 2013/0171599 A1 | 7/2013 | Bleich et al. |
| 2013/0179112 A1 | 7/2013 | Ma et al. |
| 2013/0190903 A1 | 7/2013 | Balakrishnan et al. |
| 2013/0312589 A1 | 11/2013 | MacPherson |
| 2014/0213920 A1 | 7/2014 | Lee et al. |
| 2015/0080746 A1 | 3/2015 | Bleich et al. |
| 2015/0142147 A1 | 5/2015 | Stanghed et al. |
| 2015/0182149 A1 | 7/2015 | Rapoport et al. |
| 2015/0285659 A1 | 10/2015 | Curtis et al. |
| 2016/0051167 A1 | 2/2016 | Saha et al. |
| 2016/0093107 A1 | 3/2016 | Yamamoto et al. |

OTHER PUBLICATIONS

U.S. Appl. No. 14/883,245, filed Oct. 14, 2015 for "Heart Rate Control Based Upon Media Content Selection".

U.S. Appl. No. 14/883,232, filed Oct. 14, 2015 for "Cadence Determination and Media Content Selection".

U.S. Appl. No. 14/883,298, filed Oct. 14, 2015 for "Cadence-Based Playlists Management System".

U.S. Appl. No. 14/883,273, filed Oct. 14, 2015 for "Multi-Track Playback of Media Content During Repetitive Motion Activities".

U.S. Appl. No. 14/883,295, filed Oct. 14, 2015 for "Search Media Content Based Upon Tempo".

U.S. Appl. No. 14/883,252, filed Oct. 14, 2015 for "Repetitive Motion Activity Enhancement Based Upon Media Content Selection".

U.S. Appl. No. 14/944,972, filed Nov. 18, 2015 for "System for Managing Transitions Between Media Content Items".

U.S. Appl. No. 14/945,008, filed Nov. 18, 2015 for "Identifying Media Content".

U.S. Appl. No. 14/883,323, filed Oct. 14, 2015 for "Accessibility Management System for Media Content Items".

U.S. Appl. No. 14/883,336, filed Oct. 14, 2015 for "Selection and Playback of Song Versions Using Cadence".

Office Action from U.S. Appl. No. 14/883,232, dated May 5, 2016, 23 pages.

International Search Report and Written Opinion from related International Patent Application No. PCT/EP2016/061047, dated Aug. 9, 2016, 11 pages.

CADENCE AND MEDIA CONTENT PHASE ALIGNMENT

CROSS-REFERENCE TO RELATED APPLICATION

This application is a continuation of U.S. Ser. No. 14/883,318, filed Oct. 14, 2015, which claims priority to U.S. Ser. No. 62/163,856 filed on May 19, 2015 and entitled CADENCE AND MEDIA CONTENT PHASE ALIGNMENT, the disclosures of which are hereby incorporated by reference in their entirety.

BACKGROUND

Running, as well as many other recreation or fitness activities, include repetitive motions. For example, running and walking involve repetitive steps, biking involves repetitive rotational movements, rowing involves repetitive strokes, and swimming involves repetitive strokes and kicks. There are of course many other recreation and fitness activities that also include various repetitive motions. These repetitive motion activities may be performed in place (e.g., using a treadmill, stationary bike, rowing machine, swimming machine, etc.) or in motion (e.g., on roads, trails, or tracks or in a pool or body of water, etc.). Cadence refers to the frequency of these repetitive motions and is often measured in terms of motions per minute (e.g., steps per minute, rotations per minute, strokes per minute, or kicks per minute).

Many people enjoy consuming media content, such as listening to audio content or watching video content, while running or engaging in other repetitive-motion activities. Examples of audio content include songs, albums, podcasts, audiobooks, etc. Examples of video content include movies, music videos, television episodes, etc. Using a mobile phone or other media-playback device a person can access large catalogs of media content. For example, a user can access an almost limitless catalog of media content through various free and subscription-based streaming services. Additionally, a user can store a large catalog of media content on his or her mobile device.

This nearly limitless access to media content introduces new challenges for users. For example, it may be difficult to find or select the right media content and playback the selected media content in a manner that complements a particular moment during a run or other repetitive-motion activity.

SUMMARY

In general terms, this disclosure is directed to cadence and media content phase alignment. In one possible configuration and by non-limiting example, a media-playback device acquires a cadence associated with a repetitive-motion activity and aligns playback of media content to a repetitive-motion activity that the user is engaging in. Various aspects are described in this disclosure, which include, but are not limited to, the following aspects.

In one aspect, a media-playback device for playing back media content for a user performing a repetitive-motion activity, the media-playback device comprising: a content output device that operates to output media content; a cadence-acquiring device comprising a movement-determining device and a cadence-determination engine configured to determine a cadence based on movement data captured by the movement-determining device; a phase-delay calibration engine configured to determine phase delay values for at least one cadence value; a cadence-based media content selection engine configured to identify a media content item based on the cadence determined by the cadence-acquiring device, wherein the media content item comprises music with a tempo that corresponds to the cadence; and a phase-aligned media playback engine configured to: align the identified media content item to the repetitive-motion activity; and cause the media-output device to output the aligned media content item.

In another aspect, a method of cadence-based media playback for use during repetitive-motion activities comprising: determining a cadence associated with a repetitive-motion activity based on acceleration data captured by a plurality of accelerometers, wherein the acceleration data comprises sequences of acceleration sample data captured from each of the plurality of accelerometers over a duration of time; identifying a media content item based on the determined cadence; phase aligning the identified media content item to the repetitive-motion activity; and playing back the aligned media content item.

A method of calibrating a cadence-based media playback for use during repetitive-motion activities comprising: generating media output, wherein the media output has a tempo; determining a cadence associated with a repetitive-motion activity based on acceleration data captured by a plurality of accelerometers, wherein the acceleration data comprises sequences of acceleration sample data captured from each of the plurality of accelerometers over a duration of time; determining whether the tempo of the media output corresponds to the determined cadence; and upon determining that the tempo of the media output corresponds to the determined cadence, calculating a phase delay value for the determined cadence based on an action point within the repetitive-motion activity and a beat within the media output.

DETAILED DESCRIPTION

Figure 1:
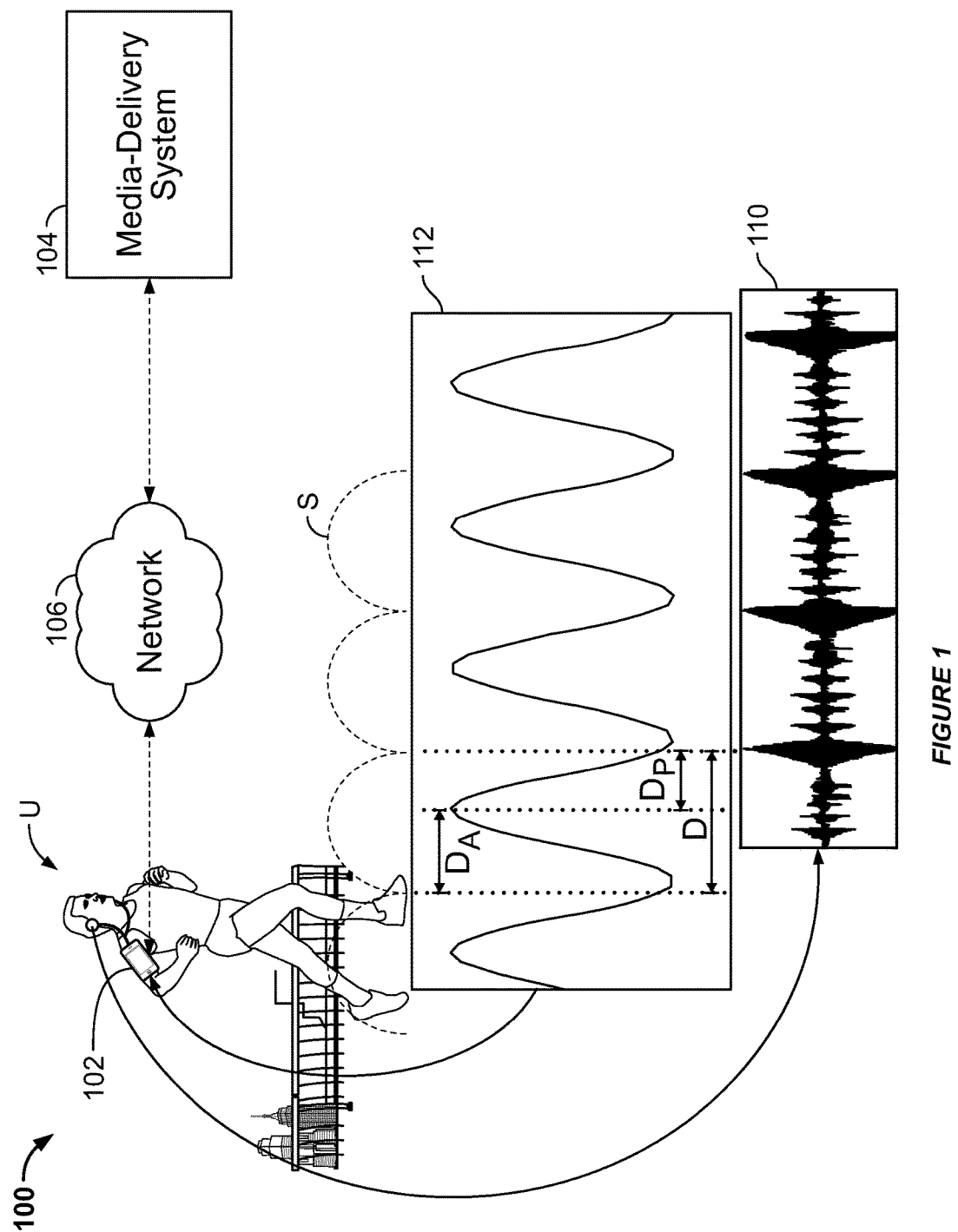
FIG. 1 illustrates an example system for cadence and media content phase alignment.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Users of media-playback devices often consume media content while engaging in various activities, including repetitive motion activities. As noted above, examples of repetitive-motion activities may include swimming, biking, running, rowing, and other activities. Consuming media content may include one or more of listening to audio content, watching video content, or consuming other types of media content. For ease of explanation, the embodiments described in this application are presented using specific examples. For example, audio content (and in particular music) is described as an example of one form of media consumption. As another example, running is described as one example of a repetitive-motion activity. However, it should be understood that the same concepts are equally applicable to other forms of media consumption and to other forms of repetitive-motion activities, and at least some embodiments include other forms of media consumption and/or other forms of repetitive-motion activities.

The users may desire that the media content fits well with the particular repetitive-motion activity. For example, a user who is running may find it more desirable to listen to music with a beat that corresponds to the user's cadence. Beneficially, by matching the beat of the music to the cadence, the user's performance or enjoyment of the repetitive-motion activity may be enhanced. The user's enjoyment may be further enhanced if the music begins playing with the beat aligned to the cadence (e.g., the beat occurs concurrently with each foot strike). By beginning playback in an aligned manner, the user will not need to adjust his or her activity to align with the music. This desire cannot be met with traditional media-playback devices and media-delivery systems.

FIG. 1 illustrates an example system 100 for cadence and media content phase alignment. The example system 100 includes a media-playback device 102 and a media-delivery system 104. The system 100 communicates across a network 106. Also shown is media output 110 generated by the media-playback device 102 and acceleration signal 112 generated by some embodiments of the media-playback device 102. In addition, a user U who is running is also shown. The user U's upcoming steps S are shown as well. A step represents a single strike of the runner's foot upon the ground.

The media-playback device 102 operates to play media content items to produce media output 110. In at least some embodiments, the media-playback device 102 also operates to capture the acceleration signal 112 related to the acceleration of the media-playback device 102. As explained in more detail below, in some embodiments, the acceleration signal 112 is generated from sequential measurements captured by one or more accelerometers in the media-playback device 102. For example, the acceleration signal may be generated by filtering the signal from the accelerometer with measurements having the highest energy.

In some embodiments, the media content items are provided by the media-delivery system 104 and transmitted to the media-playback device 102 using the network 106. A media content item is an item of media content, including audio, video, or other types of media content, which may be stored in any format suitable for storing media content. Non-limiting examples of media content items include songs, albums, music videos, movies, television episodes, podcasts, other types of audio or video content, and portions or combinations thereof.

The media-playback device 102 plays media content for the user based on the user's cadence. In the example shown, the media output 110 includes music with a tempo that corresponds to the user's cadence. The tempo (or rhythm) of music refers to the frequency of the beat and is typically measured in beats per minute (BPM). The beat is the basic unit of rhythm in a musical composition (as determined by the time signature of the music). Accordingly, in the example shown, the user U's steps occur at the same frequency as the beat of the music. Fur For example, if the user U is running at a cadence of 180 steps per minute, the media-playback device 102 may play a media content item having a tempo equal to or approximately equal to 180 BPM. In other embodiments, the media-playback device 102 plays a media content item having a tempo equal or approximately equal to the result of dividing the cadence by an integer such as a tempo that is equal to or approximately equal to one-half (e.g., 90 BPM when the user is running at a cadence of 180 steps per minute), one-fourth, or one-eighth of the cadence. Alternatively, the media-playback device 102 plays a media content item having a tempo that is equal or approximately equal to an integer multiple (e.g., 2×, 4×, etc.) of the cadence. Further, in some embodiments, the media-playback device 102 operates to play multiple media content items including one or more media content items having a tempo equal to or approximately equal to the cadence and one or more media content items have a tempo equal or approximately equal to the result of multiplying or dividing the cadence by an integer. Various other combinations are possible as well.

In some embodiments, the media-playback device 102 operates to play music having a tempo that is within a predetermined range of a target tempo. In at least some embodiments, the predetermined range is plus or minus 2.5 BPM. For example, if the user U is running at a cadence of 180 steps per minute, the media-playback device 102 operates to play music having a tempo of 177.5-182.5 BPM. Alternatively, in other embodiments, the predetermined range is itself in a range from 1 BPM to 10 BPM.

Further, in some embodiments, the media-playback device 102 operates to play music having a tempo equal to or approximately equal to a user U's cadence after it is rounded. For example, the cadence may be rounded to the nearest multiple of 2.5, 5, or 10 and then the media-playback device 102 plays music having a tempo equal to or approximately equal to the rounded cadence. In yet other embodiments, the media-playback device 102 uses the cadence to select a predetermined tempo range of music for playback. For example, if the user U's cadence is 181 steps per minute, the media-playback device 102 may operate to play music from a predetermined tempo range of 180-184.9 BPM; while if the user U's cadence is 178 steps per minute, the media-playback device 102 may operate to play music from a predetermined tempo range of 175-179.9 BPM.

In addition, in at least some embodiments, the media-playback device 102 operates to align the playback of media content so that the beat of the music is output (or heard) concurrently with a particular action point within the repetitive motion. Examples of the action point include the foot strike in running, the start of a downstroke of the pedal in biking, the start of kick or pull in swimming, and the start of a pull in rowing. As noted previously, for ease of explanation, the embodiments described in this application are presented using specific examples. For example, foot strikes within running are described as an example of an action point within a repetitive-motion activity. However, it should be understood that the same concepts are equally applicable to other action points and other forms of repetitive-motion activities.

FIG. 1 illustrates an example alignment of the media output 110 to the steps S (e.g., the highest spikes in the musical signal are aligned with the foot strikes of steps S). In order to align the media output 110 to the steps S, some embodiments determine a delay D associated with the time required to detect that the User U's foot has struck the ground and the time required to output a corresponding beat. Additionally, in at least some embodiments, the delay D is further associated with the time required for the sound of the beat to be perceive by the user U. In some embodiments, the delay D includes an acquisition delay $D_A$ and a production delay $D_P$.

The acquisition delay $D_A$ relates to the various delays associated with detecting the occurrence of the foot strike.

An additional complication related to the acquisition delay $D_A$ is determining which portion of the acceleration signal 112 corresponds to a foot strike (or other action point). As described elsewhere herein, the acceleration signal 112 includes a wave that oscillates with a frequency that corresponds to the cadence. But the wave position within the acceleration signal 112 that correspond to a foot strike (or other action point) will vary depending on the physical orientation of the media-playback device 102. For purposes of clarity, the wave positions that correspond to an action point of a repetitive motion will be referred to as wave action positions. Example methods of identifying wave action positions in an acceleration signal are described with respect to at least FIG. 9.

In some embodiments, the acquisition delay $D_A$ may include a physical delay, a hardware delay, and a filtering delay. Other embodiments include additional, different, or fewer delays. The physical delay relates to the time required for the physical signal to reach the media-playback device 102 and is affected by how the media-playback device 102 is carried. For example, if the user is holding the media-playback device 102 in his or her hand while running, there will be a certain physical delay between when the user's foot strikes the ground and when the media-playback device 102 changes direction. Furthermore, that physical delay will be different if the user U is carrying the media-playback device 102 in a different way (e.g., in a pants pocket instead).

The hardware delay relates to the time required for the hardware (e.g., accelerometers and other components) to detect the change in acceleration that corresponds to wave action position (e.g., a foot strike). The filter delay corresponds to the delay associated with filtering the acceleration signal to identify signals in a frequency range associated with the expected cadence. In some embodiments, the filter delay is variable and relates to the frequency at which the filter operates. In some embodiments, the filter delay is calculated mathematically. Additionally, in some embodiments, the filter delay is not separately determined but is instead addressed with a calibration process that compensates for the delay D (which includes the filter delay as well as multiple other delays as well).

The production delay $D_P$ relates to the various delays associated with the media content reaching the user after the media-playback device 102 determines to output the media content (e.g., begins to execute instructions to playback the media content). In some embodiments, the production delay $D_P$ includes a media content retrieval delay and an audio pipeline delay. The media content retrieval delay corresponds to the time required to retrieve the media content item that will be output. In some embodiments, the media content retrieval delay is dependent on the performance of the network 106 (e.g., when retrieving streaming media, etc.). In some embodiments, the retrieval delay relates to finding or accessing a media content item locally. The audio pipeline delay relates to the delay required to transmit the media output to the user. In some embodiments, the audio pipeline delay is a function of operating system activity on the media-playback device.

In some embodiments, the production delay $D_P$ does not include a media content. Instead, the media-playback device 102 buffers the media content before beginning playback. Beneficially by buffering the media content, at least one potential source of variability in the delay D is minimized or eliminated. Buffering the media content may be particularly beneficial in embodiments that stream media content over a network that has variable and unpredictable quality.

Some embodiments calculate the delay D for one or more cadence, users, or physical configurations as described in greater detail herein. Then the calculated delay D is used during playback to shift media content items relative to the acceleration signal 112 in order to align media output 110 to the foot strikes in the user's steps S. For example, in some embodiments, media content items are annotated with the location of one or more of beats, downbeats, upbeats, etc. In some embodiments, the media-playback device 102 operates to playback a media content item such that the beat is played in advance of the next expected wave action point (corresponding to a foot strike) by a time period equal to the delay D. In this manner, the user U's foot will be striking the ground when the beat actually reaches the user U.

Figure 2:
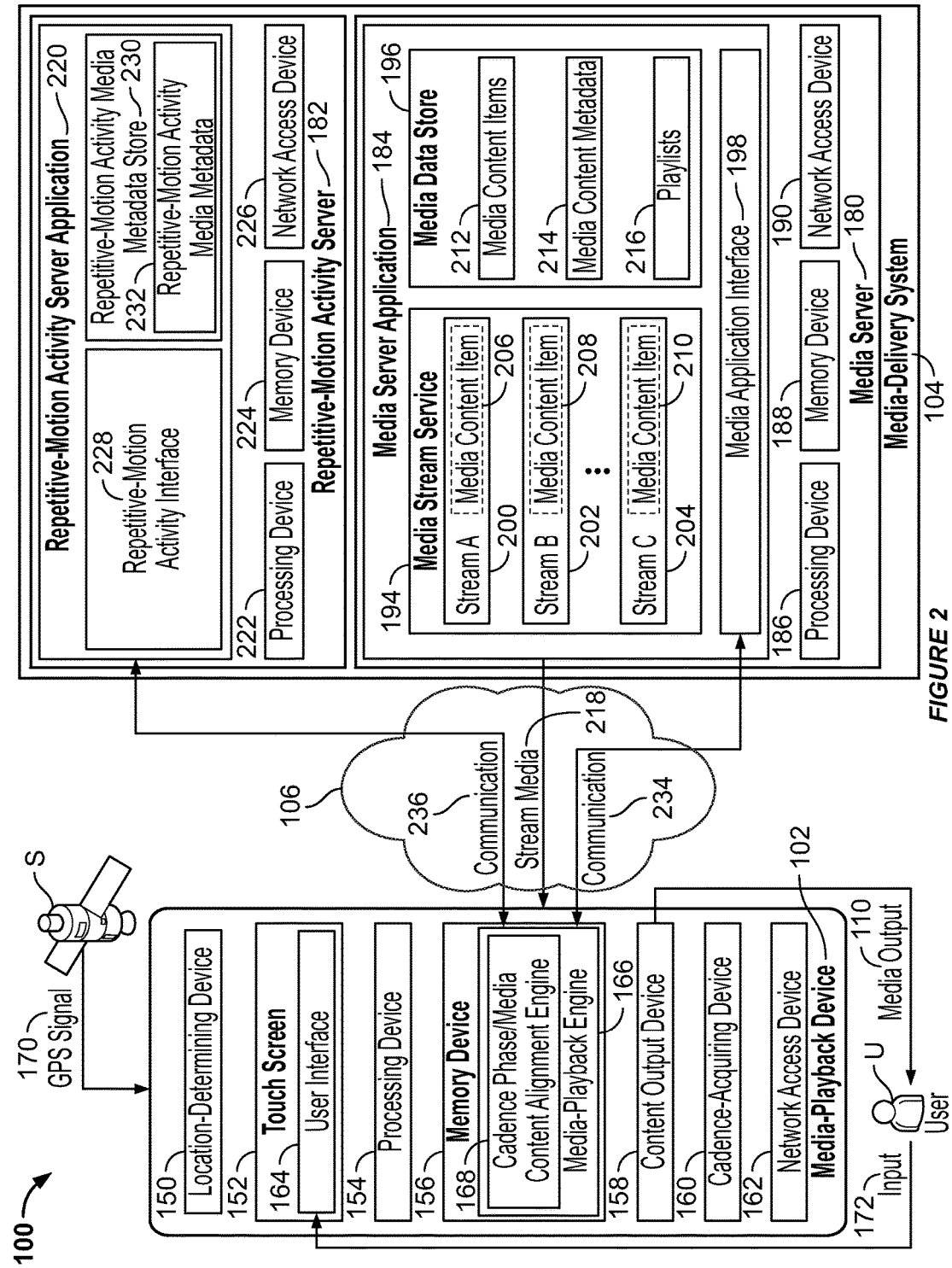
FIG. 2 is a schematic illustration of the example system of FIG. 1.

FIG. 2 is a schematic illustration of an example system 100 for cadence and media content phase alignment. In FIG. 2, the media-playback device 102, the media-delivery system 104, and the network 106 are shown. Also shown are the user U and a satellite S.

As noted above, the media-playback device 102 operates to play media content items. In some embodiments, the media-playback device 102 operates to play media content items that are provided (e.g., streamed, transmitted, etc.) by a system external to the media-playback device such as the media-delivery system 104, another system, or a peer device. Alternatively, in some embodiments, the media-playback device 102 operates to play media content items stored locally on the media-playback device 102. Further, in at least some embodiments, the media-playback device 102 operates to play media content items that are stored locally as well as media content items provided by other systems.

In some embodiments, the media-playback device 102 is a computing device, handheld entertainment device, smartphone, tablet, watch, wearable device, or any other type of device capable of playing media content. In yet other embodiments, the media-playback device 102 is a laptop computer, desktop computer, television, gaming console, set-top box, network appliance, blue-ray or DVD player, media player, stereo, or radio.

In at least some embodiments, the media-playback device 102 includes a location-determining device 150, a touch screen 152, a processing device 154, a memory device 156, a content output device 158, a cadence-acquiring device 160, and a network access device 162. Other embodiments may include additional, different, or fewer components. For example, some embodiments may include a recording device such as a microphone or camera that operates to record audio or video content. As another example, some embodiments do not include one or more of the location-determining device 150 and the touch screen 152.

The location-determining device 150 is a device that determines the location of the media-playback device 102. In some embodiments, the location-determining device 150 uses one or more of the following technologies: Global Positioning System (GPS) technology which may receive GPS signals 170 from satellites S, cellular triangulation technology, network-based location identification technology, Wi-Fi positioning systems technology, and combinations thereof.

The touch screen 152 operates to receive an input 172 from a selector (e.g., a finger, stylus etc.) controlled by the user U. In some embodiments, the touch screen 152 operates as both a display device and a user input device. In some embodiments, the touch screen 152 detects inputs based on one or both of touches and near-touches. In some embodiments, the touch screen 152 displays a user interface 164 for interacting with the media-playback device 102. As noted above, some embodiments do not include a touch screen 152. Some embodiments include a display device and one or more separate user interface devices. Further, some embodiments do not include a display device.

In some embodiments, the processing device 154 comprises one or more central processing units (CPU). In other embodiments, the processing device 154 additionally or alternatively includes one or more digital signal processors, field-programmable gate arrays, or other electronic circuits.

The memory device 156 operates to store data and instructions. In some embodiments, the memory device 156 stores instructions for a media-playback engine 166 that includes a cadence and media content phase alignment engine 168. In some embodiments, the media-playback engine 166 operates to playback media content and the cadence and media content phase alignment engine 168 operates to align the playback of media content to a repetitive-motion activity.

The memory device 156 typically includes at least some form of computer-readable media. Computer readable media includes any available media that can be accessed by the media-playback device 102. By way of example, computer-readable media include computer readable storage media and computer readable communication media.

Computer readable storage media includes volatile and nonvolatile, removable and non-removable media implemented in any device configured to store information such as computer readable instructions, data structures, program modules, or other data. Computer readable storage media includes, but is not limited to, random access memory, read only memory, electrically erasable programmable read only memory, flash memory and other memory technology, compact disc read only memory, blue ray discs, digital versatile discs or other optical storage, magnetic cassettes, magnetic tape, magnetic disk storage or other magnetic storage devices, or any other medium that can be used to store the desired information and that can be accessed by the media-playback device 102. In some embodiments, computer readable storage media is non-transitory computer readable storage media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The content output device 158 operates to output media content. In some embodiments, the content output device 158 generates media output 110 for the user U. Examples of the content output device 158 include a speaker, an audio output jack, a Bluetooth transmitter, a display panel, and a video output jack. Other embodiments are possible as well. For example, the content output device 158 may transmit a signal through the audio output jack or Bluetooth transmitter that can be used to reproduce an audio signal by a connected or paired device such as headphones or a speaker.

The cadence-acquiring device 160 operates to acquire a cadence associated with the user U. In at least some embodiments, the cadence-acquiring device 160 operates to determine cadence directly and includes one or more accelerometers or other motion-detecting technologies. Alternatively, the cadence-acquiring device 160 operates to receive data representing a cadence associated with the user U. For example, in some embodiments, the cadence-acquiring device 160 operates to receive data from a watch, bracelet, foot pod, chest strap, shoe insert, anklet, smart sock, bicycle computer, exercise equipment (e.g., treadmill, rowing machine, stationary cycle), or other device for determining or measuring cadence. Further, in some embodiments, the cadence-acquiring device 160 operates to receive a cadence value input by the user U or another person.

The network access device 162 operates to communicate with other computing devices over one or more networks, such as the network 106. Examples of the network access device include wired network interfaces and wireless network interfaces. Wireless network interfaces includes infrared, BLUETOOTH® wireless technology, 802.11a/b/g/n/ac, and cellular or other radio frequency interfaces in at least some possible embodiments.

The network 106 is an electronic communication network that facilitates communication between the media-playback device 102 and the media-delivery system 104. An electronic communication network includes a set of computing devices and links between the computing devices. The computing devices in the network use the links to enable communication among the computing devices in the network. The network 106 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 106 includes various types of links. For example, the network 106 can include wired and/or wireless links, including Bluetooth, ultra-wideband (UWB), 802.11, ZigBee, cellular, and other types of wireless links. Furthermore, in various embodiments, the network 106 is implemented at various scales. For example, the network 106 can be implemented as one or more local area networks (LANs), metropolitan area networks, subnets, wide area networks (such as the Internet), or can be implemented at another scale. Further, in some embodiments, the network 106 includes multiple networks, which may be of the same type or of multiple different types.

The media-delivery system 104 comprises one or more computing devices and operates to provide media content items to the media-playback devices 102 and, in some embodiments, other media-playback devices as well. The media-delivery system 104 includes a media server 180 and a repetitive-motion activity server 182. In at least some embodiments, the media server 180 and the repetitive-motion activity server 182 are provided by separate computing devices. In other embodiments, the media server 180 and the repetitive-motion activity server 182 are provided by the same computing devices. Further, in some embodiments, one or both of the media server 180 and the repetitive-motion activity server 182 are provided by multiple computing devices. For example, the media server 180 and the repetitive-motion activity server 182 may be provided by multiple redundant servers located in multiple geographic locations.

The media server 180 operates to transmit stream media 218 to media-playback devices such as the media-playback device 102. In some embodiments, the media server 180 includes a media server application 184, a processing device 186, a memory device 188, and a network access device 190. The processing device 186, memory device 188, and network access device 190 may be similar to the processing device 154, memory device 156, and network access device 162 respectively, which have each been previously described.

In some embodiments, the media server application 184 operates to stream music or other audio, video, or other forms of media content. The media server application 184 includes a media stream service 194, a media data store 196, and a media application interface 198. The media stream service 194 operates to buffer media content such as media content items 206, 208, and 210, for streaming to one or more streams 200, 202, and 204.

The media application interface 198 can receive requests or other communication from media-playback devices or other systems, to retrieve media content items from the media server 180. For example, in FIG. 2, the media application interface 198 receives communication 234 from the media-playback engine 166.

In some embodiments, the media data store 196 stores media content items 212, media content metadata 214, and playlists 216. The media data store 196 may comprise one or more databases and file systems. Other embodiments are possible as well. As noted above, the media content items 212 may be audio, video, or any other type of media content, which may be stored in any format for storing media content.

The media content metadata 214 operates to provide various information associated with the media content items 212. In some embodiments, the media content metadata 214 includes one or more of title, artist name, album name, length, genre, mood, era, etc. In addition, in some embodiments, the media content metadata 214 includes annotation data for the media content item, such as the temporal location of the beat in music included in the media content item. The playlists 216 operate to identify one or more of the media content items 212 and. In some embodiments, the playlists 216 identify a group of the media content items 212 in a particular order. In other embodiments, the playlists 216 merely identify a group of the media content items 212 without specifying a particular order. Some, but not necessarily all, of the media content items 212 included in a particular one of the playlists 216 are associated with a common characteristic such as a common genre, mood, or era.

The repetitive-motion activity server 182 operates to provide repetitive-motion activity—specific information about media content items to media-playback devices. In some embodiments, the repetitive-motion activity server 182 includes a repetitive-motion activity server application 220, a processing device 222, a memory device 224, and a network access device 226. The processing device 222, memory device 224, and network access device 226 may be similar to the processing device 154, memory device 156, and network access device 162 respectively, which have each been previously described.

In some embodiments, repetitive-motion activity server application 220 operates to transmit information about the suitability of one or more media content items for playback during a particular repetitive-motion activity. The repetitive-motion activity server application 220 includes a repetitive-motion activity interface 228 and a repetitive-motion activity media metadata store 230.

In some embodiments, the repetitive-motion activity server application 220 may provide a list of media content items at a particular tempo to a media-playback device in response to a request that includes a particular cadence value. Further, in some embodiments, the media content items included in the returned list will be particularly relevant for the repetitive-motion activity in which the user is engaged (for example, if the user is running, the returned list of media content items may include only media content items that have been identified as being highly runnable).

The repetitive-motion activity interface 228 operates to receive requests or other communication from media-playback devices or other systems to retrieve information about media content items from the repetitive-motion activity server 182. For example, in FIG. 2, the repetitive-motion activity interface 228 receives communication 236 from the media-playback engine 166.

In some embodiments, the repetitive-motion activity media metadata store 230 stores repetitive-motion activity media metadata 232. The repetitive-motion activity media metadata store 230 may comprise one or more databases and file systems. Other embodiments are possible as well.

The repetitive-motion activity media metadata 232 operates to provide various information associated with media content items, such as the media content items 212. In some embodiments, the repetitive-motion activity media metadata 232 provides information that may be useful for selecting for or playing back media content items for a repetitive-motion activity. For example, in some embodiments, the repetitive-motion activity media metadata 232 stores runnability scores for media content items that correspond to the suitability of particular media content items for playback during running. As another example, in some embodiments, the repetitive-motion activity media metadata 232 stores timestamps (e.g., start and end points) that identify portions of a media content items that are particularly well-suited for playback during running (or another repetitive-motion activity).

Each of the media-playback device 102 and the media-delivery system 104 can include additional physical computer or hardware resources. In at least some embodiments, the media-playback device 102 communicates with the media-delivery system 104 via the network 106.

Although in FIG. 2 only a single media-playback device 102 and media-delivery system 104 are shown, in accordance with some embodiments, the media-delivery system 104 can support the simultaneous use of multiple media-playback devices, and the media-playback device can simultaneously access media content from multiple media-delivery systems. Additionally, although FIG. 2 illustrates a streaming media based system for cadence and media content phase alignment, other embodiments are possible as well. For example, in some embodiments, the media-playback device 102 includes a media data store 196 and the media-playback device 102 is configured to perform cadence and media content phase alignment without accessing the media-delivery system 104. Further in some embodiments, the media-playback device 102 operates to store previously streamed media content items in a local media data store.

In at least some embodiments, the media-delivery system 104 can be used to stream, progressively download, or otherwise communicate music, other audio, video, or other forms of media content items to the media-playback device 102 based on a cadence acquired by the cadence-acquiring device 160 of the media-playback device 102. In accordance with an embodiment, a user U can direct the input 172 to the user interface 164 to issue requests, for example, to playback media content corresponding to the cadence of a repetitive-motion activity on the media-playback device 102.

Figure 3:
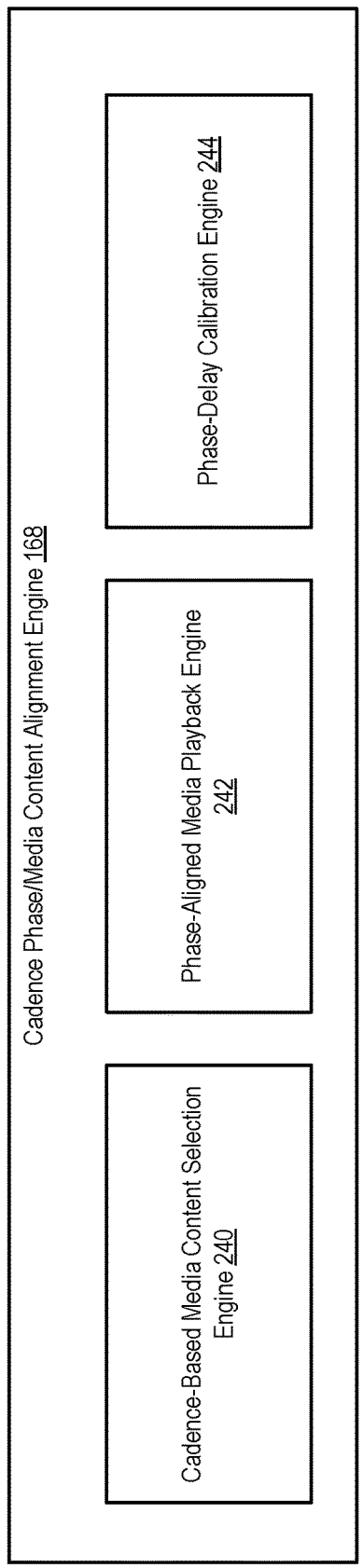
FIG. 3 is a schematic block diagram of the cadence and media content phase alignment engine of FIG. 2.

FIG. 3 is a schematic block diagram of the cadence and media content phase alignment engine 168. In some embodiments, the cadence and media content phase alignment engine 168 includes a cadence-based media content selection engine 240, a phase-aligned media playback engine 242 and a phase-delay calibration engine 244.

The cadence-based media content selection engine 240 operates to select media content for playback based on a cadence. The phase-aligned media playback engine 242 operates to playback media content and to align playback of media content to the repetitive-motion activity of the user, such as by aligning the beat of music included in the media content with the foot strikes of the user. The phase-delay calibration engine 244 operates to calibrate the media-playback device 102 for performing alignment for a particular user performing a particular repetitive-motion activity.

Figure 4:
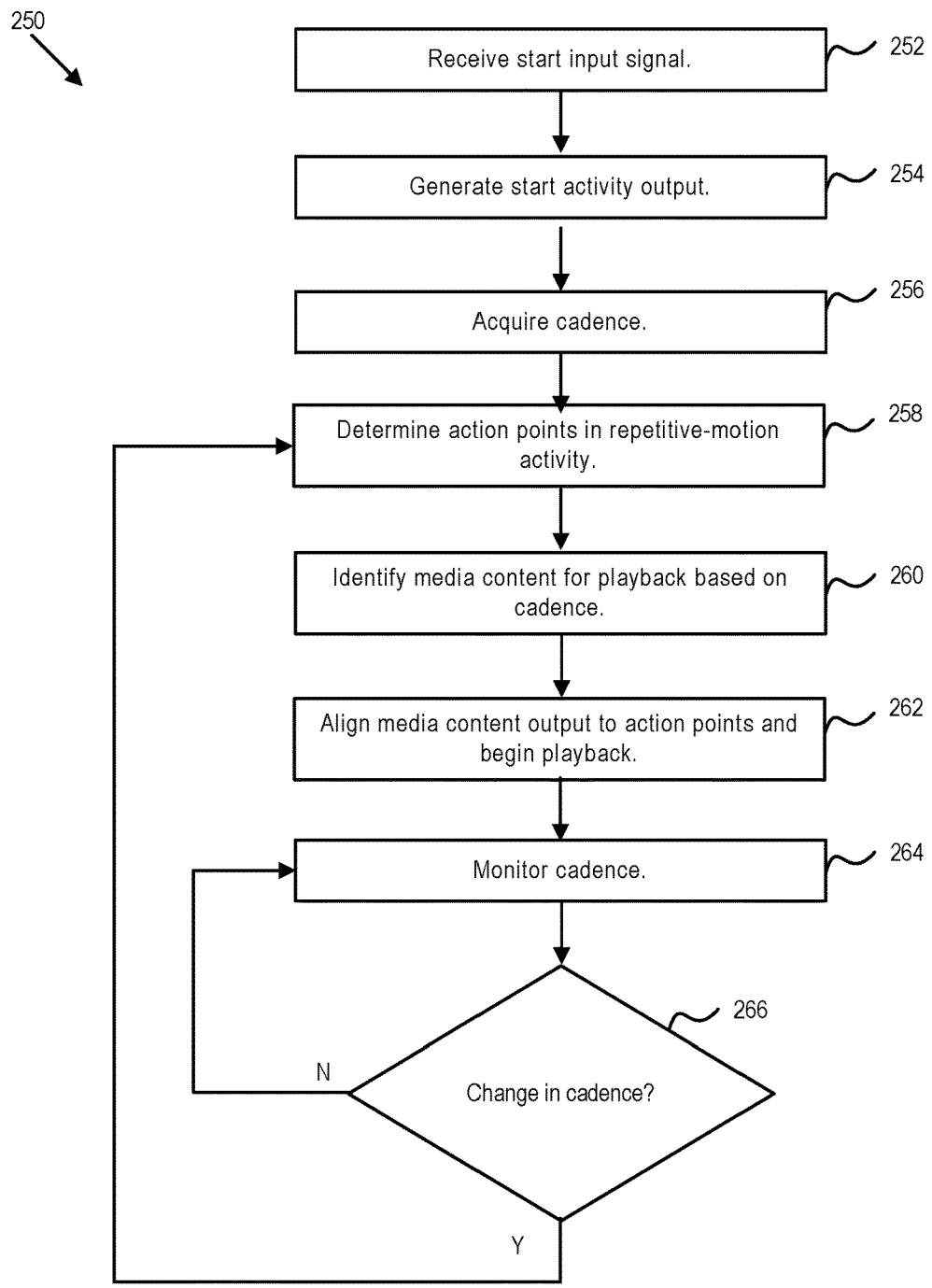
FIG. 4 illustrates an example method of cadence and media content phase alignment performed by some embodiments of the media-playback device of FIG. 1.

FIG. 4 illustrates an example method 250 of cadence and media content phase alignment performed by some embodiments of the media-playback device 102.

At operation 252, a start input signal is received by the media-playback device 102. In at least some embodiments, the start input signal is received from a user and operates to indicate that the user desires to start media playback to accompany a repetitive-motion activity. Various embodiments operate to receive various start input signals. Example start input signals include a touch input from a selector on a particular location on the user interface 164 (e.g., a start button), a spoken command captured by a microphone or otherwise, or a movement that is detected by the media-playback device 102 such as the user beginning to run while holding the media-playback device 102.

At operation 254, a start activity output is generated. In at least some embodiments, the start activity output operates to communicate to the user that the user should begin running (or a different repetitive-motion activity). Various embodiments generate one or more start activity outputs. Examples of start activity outputs include generation of audible signals such as beeps, bells, sound effects, pre-recorded voiceovers (e.g., "Go," "Start Running," or "Start Activity"), etc. Other example of start activity outputs include visual indicators on the user interface 164.

At operation 256, a cadence associated with a repetitive-motion activity of the user is acquired. In some embodiments, the cadence is acquired by determining the cadence based on movements of the media-playback device 102 (e.g., using the methods illustrated and described with respect to at least FIGS. 5-8). In other embodiments, the cadence is acquired from a separate device, from a user input, or otherwise. Regardless of how the cadence is acquired, once that cadence is acquired, the method 250 continues to operation 258. Additionally, some embodiments generate a cadence acquired output upon determining the cadence (such as a sound or visual indicator).

At operation 258, the action points in the repetitive-motion activity are determined. In at least some embodiments, the action points are determined by analyzing an acceleration signal of the media-playback device 102 to identify wave action positions corresponding to the action points.

At operation 260, one or multiple media content items (e.g., a playlist) are identified for playback by the media-playback device 102 based on the acquired cadence. In some embodiments, the media content items include music with a tempo that corresponds to the cadence. The identified media content items can be stored locally in a file or streamed from an external source such as the media-delivery system 104. For example, in some embodiments, the media-playback device 102 requests media content items that correspond to the acquired cadence.

At operation 262, the identified media content is aligned with the identified action points and the aligned media content is played for the user. In some embodiments, a predetermined delay value is used to align the beats of music included in the identified media content to the action points corresponding to the user's steps. In some embodiments, the predetermined delay value is calculated using one or more of the methods illustrated and described with respect to at least FIGS. 9-11.

At operation 264, the cadence is monitored. In some embodiments, the cadence is monitored by continuing to detect the cadence associated with a repetitive movement of the media-playback device 102. In other embodiments, the cadence is monitored by continuing to acquire a cadence from a separate device, a user input, or otherwise.

At operation 266, it is determined whether the cadence has changed. In some embodiments, the cadence is determined to have changed when the acquired cadence is different than the current cadence (i.e., the cadence used for playback of media content items) by more than a predetermined threshold. Additionally, in some embodiments, the cadence is determined to change when the acquired cadence is different than the current cadence for at least a predetermined duration (e.g., measured in terms of time, number of steps or other movements, etc.). In some embodiments, the predetermined threshold and predetermined duration are selected to distinguish intentional changes in cadence from short-term, environment-based adjustments. Examples of environment-based adjustments include slowing down to cross a street or dodge a puddle, changing cadence to traverse a staircase, changing cadence to turn, etc. In some embodiments, the intentionality of a change in cadence is determined based on a combination of the magnitude of difference and the duration of the change (e.g., a larger magnitude of difference requires a shorter duration to indicate an intentional change in cadence than a smaller magnitude of difference would, or vice versa, etc.). Additionally, some embodiments of the media-playback device 102 include an altimeter and changes in cadence that occur while the altitude measurement is changing rapidly are ignored (e.g., to ignore changes in cadence that occur while traversing a staircase, etc.). In addition, in some embodiments, changes in cadence that occur while the media-playback device 102 is changing direction are ignored. Some embodiments include a compass to determine when the media-playback device 102 is changing directions. Additionally, the location-determining device 150 is used to determine when the media-playback device 102 is changing directions in some embodiments.

If it is determined that a change in cadence has occurred the method returns to operation 258 to determine the action points in the repetitive-motion activity and continue with aligned playback of media content items identified based on the changed cadence. Additionally, in some embodiments, a cadence changed output is generated. Various embodiments generate one or more change in cadence outputs. Examples of change in cadence outputs include generation of audible signals such as beeps, bells, sound effects, pre-recorded voiceovers (e.g., "New cadence detected: 170 steps per minute"), etc. Other examples of change of cadence outputs include visual indicators that a change in cadence was detected or of the changed cadence on the user interface 164.

In some embodiments, the media content items selected for playback based on the changed cadence are immediately played back after the change in cadence is detected (with or without crossfading). In other embodiments, the media-playback device completes playback of the currently playing media content item before beginning to playback the newly selected media content items. Further, in some embodiments, the media-playback device 102 continues to playback the currently-playing media content item from a buffer until a second buffer can be sufficiently populated with stream data corresponding to the newly selected media content items.

However, if it is determined that a change in cadence has not occurred at operation 266, the method returns to operation 264, where the cadence continues to be monitored.

Figure 5:
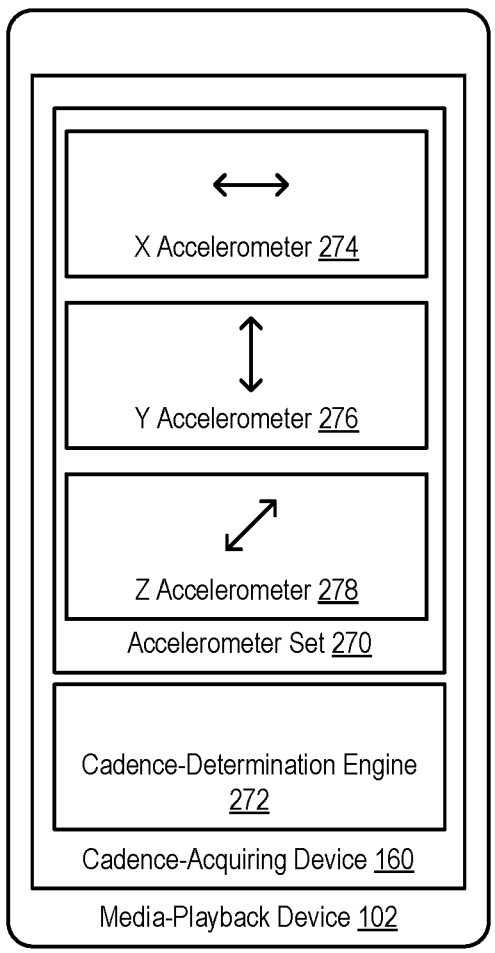
FIG. 5 illustrates an example cadence-acquiring device of FIG. 2.

FIG. 5 illustrates an example cadence-acquiring device 160. In the embodiment illustrated in FIG. 5, the cadence-acquiring device 160 operates to determine a cadence associated with a user based on movement of the media-playback device 102. In this example, the cadence-acquiring device 160 includes accelerometer set 270 and cadence-determination engine 272. Although the examples described herein use accelerometers, in other embodiments other types of movement-determining devices are used. A movement-determining device is a device that operates to capture measurements related to movement of the media-playback device. An accelerometer is an example of a movement-determining device.

The accelerometer set 270 includes at least one accelerometer. An accelerometer is a device that is used to measure acceleration, including gravitational acceleration. In some embodiments, an accelerometer measures acceleration in a single direction. In other embodiments, an accelerometer measures acceleration in more than one direction, such as in three directions. In some embodiments, the orientation of an accelerometer (and therefore the orientation of the media-playback device 102) is inferred by comparing the measured direction and magnitude of acceleration to an expected direction and magnitude of gravitational acceleration. Additionally, in some embodiments, the motion of the accelerometers is inferred from one or more measured acceleration values.

In the example shown, the accelerometer set 270 includes three accelerometers: an X accelerometer 274, a Y accelerometer 276, and a Z accelerometer 278. In this example, the X accelerometer 274 operates to measure acceleration in a horizontal direction relative to the media-playback device 102. Similarly, in this example, the Y accelerometer 276 operates to measure acceleration in a vertical direction relative to the media-playback device 102. Similarly, in this example, the Z accelerometer 278 operates to measure acceleration in a front-to-back direction relative to the media-playback device 102. In other embodiments, the accelerometer set 270 includes three accelerometers that each operate to measure acceleration in three orthogonal directions (i.e., each of the three directions is pairwise perpendicular to the other two directions). In this manner, the accelerometer set 270 operates to determine acceleration in three-dimensional space.

The cadence-determination engine 272 operates to determine a cadence based at least in part on the measurements from the accelerometer set 270. In some embodiments, the cadence-determination engine 272 analyzes sequences of measurements captured by one or more of the accelerometers. A series of measurements captured over intervals during a particular duration is an example of a sequence of measurements. An example method of determining cadence is illustrated and described with respect to at least FIG. 6.

However, as noted above, some embodiments of the cadence-acquiring device 160 do not include the accelerometer set 270 or the cadence-determination engine 272. In these embodiments, the cadence-acquiring device 160 may operate to receive a cadence value over a network from an external device or to receive a user input representing a cadence value.

Figure 6:
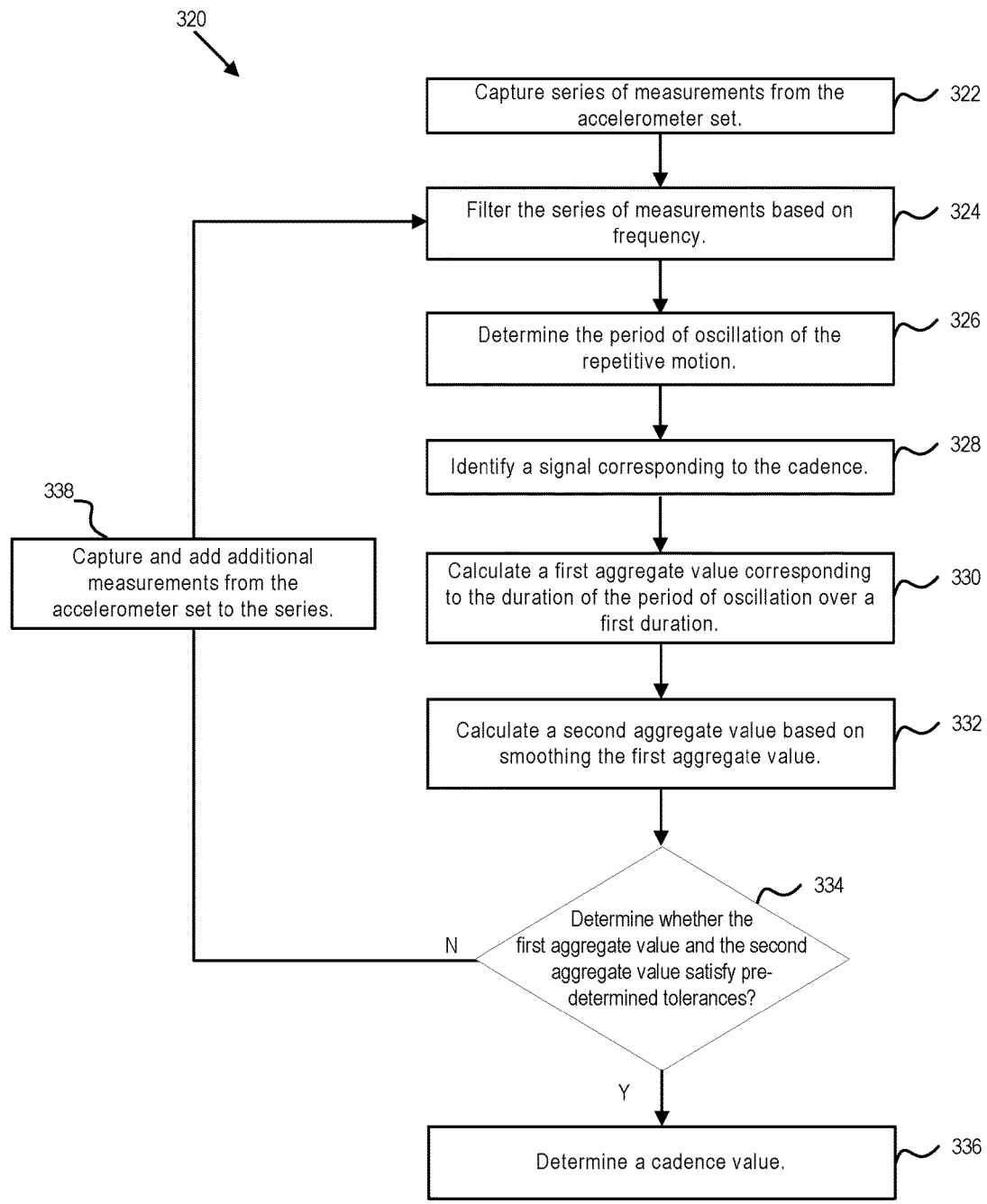
FIG. 6 illustrates an example method of determining cadence performed by some embodiments of the cadence-determination engine of FIG. 3.

FIG. 6 illustrates an example method 320 of determining cadence performed by some embodiments of the cadence-determination engine 272 using the accelerometer set 270.

At operation 322, a series of measurements is captured from one or more accelerometers of the accelerometer set 270. For purposes of this example, the method 320 will be described in the context of measurements being captured from a set of three orthogonally-oriented accelerometers. However, other embodiments capture measurements from different numbers and different configurations of accelerometers.

In at least some embodiments, the measurements are captured at a sample rate of 50 Hz. In other embodiments, the measurements are captured at a different sample rate such as a sample rate in the range of 20-200 Hz. Generally, with higher sample rates there will be less error in calculating the cadence. Other embodiments may use different sample rates, including variable sample rates, as well. In at least some embodiments, the captured samples from each accelerometer are stored as a separate series of data points.

In some embodiments, the captured measurements are amplified. For example, the acceleration measurements may be quite small when a user places the media-playback device 102 on a treadmill rather than holding it. By amplifying the captured measurements, the media-playback device 102 operates to sense a cadence from smaller vibrations transmitted through the treadmill. In some embodiments, the captured measurements are amplified if none of the signals from any of the accelerometers exceed a pre-defined threshold for a specific period of time. Furthermore, some embodiments operate to amplify the captured measurements if the location-determining device 150 indicates that the user is indoors or stationary.

At operation 324, the series of measurements are filtered based on frequency to generate filtered signals. For example, in some embodiments, each of the series are filtered with a band-pass filter such as a band-pass filter comprising third-order Butterworth filters. Beneficially, Butterworth filters provide a generally flat frequency response and thus allows for reliable energy estimation of the filtered signal. Furthermore, a third-order Butterworth filter provides a steep enough response to discard/attenuate signals outside of the desired region. Other embodiments, however, use other types of band-pass filters. For example, some embodiments use a fifth-order Butterworth filter. In some embodiments, the band-pass filter is tuned to pass the portion of the signal in the series that is likely to correspond to running (e.g., having a frequency of 140-200 steps per minute). For example, the band-pass filter may discard frequencies below 140 steps per minutes (e.g., walking, holding the media-playback device 102, etc.) and above 200 steps per minute (e.g., vibrations).

Figure 7:
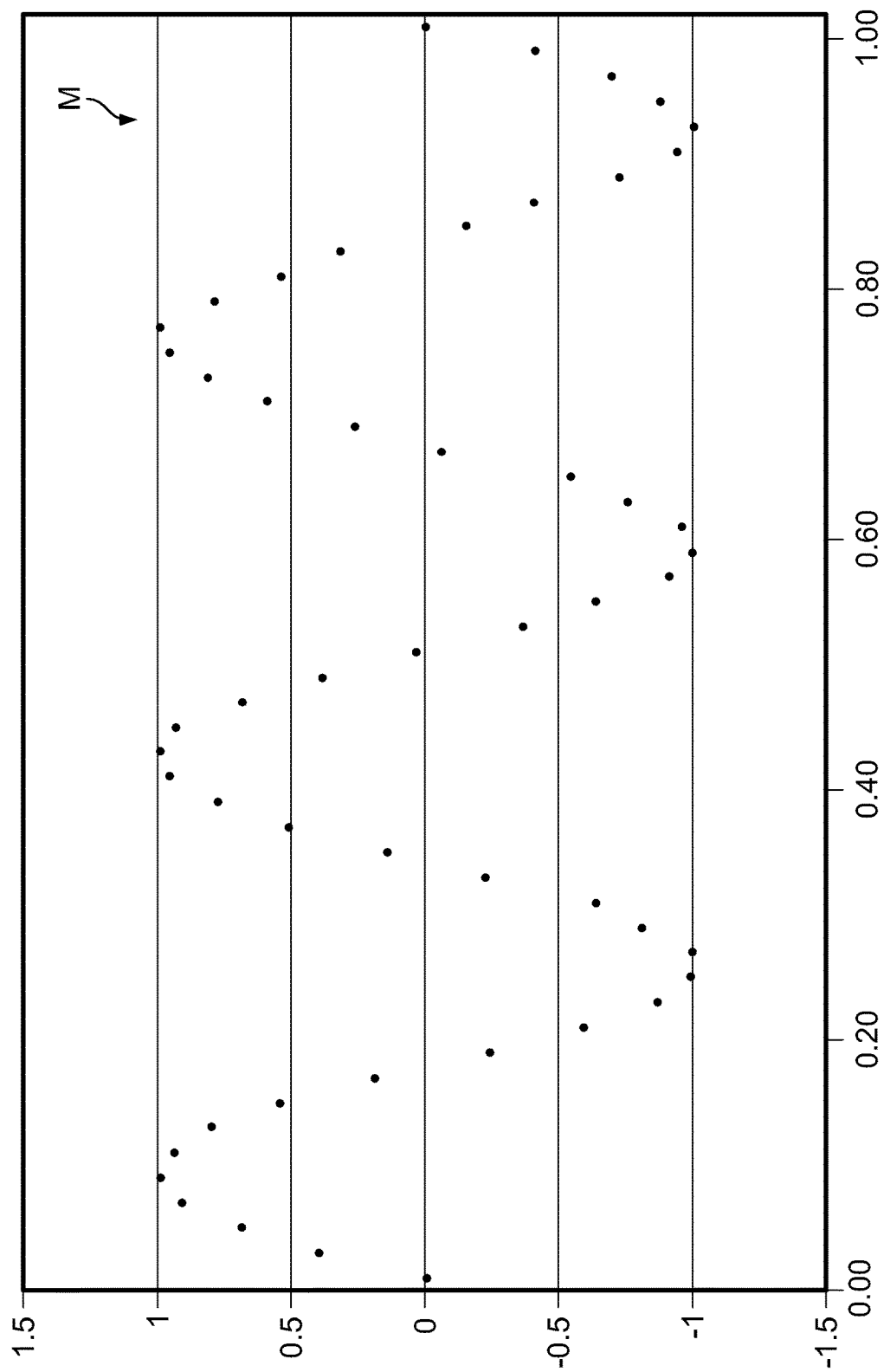
FIG. 7 shows an example series of filtered sample measurements from the accelerometer of FIG. 5.
Figure 8:
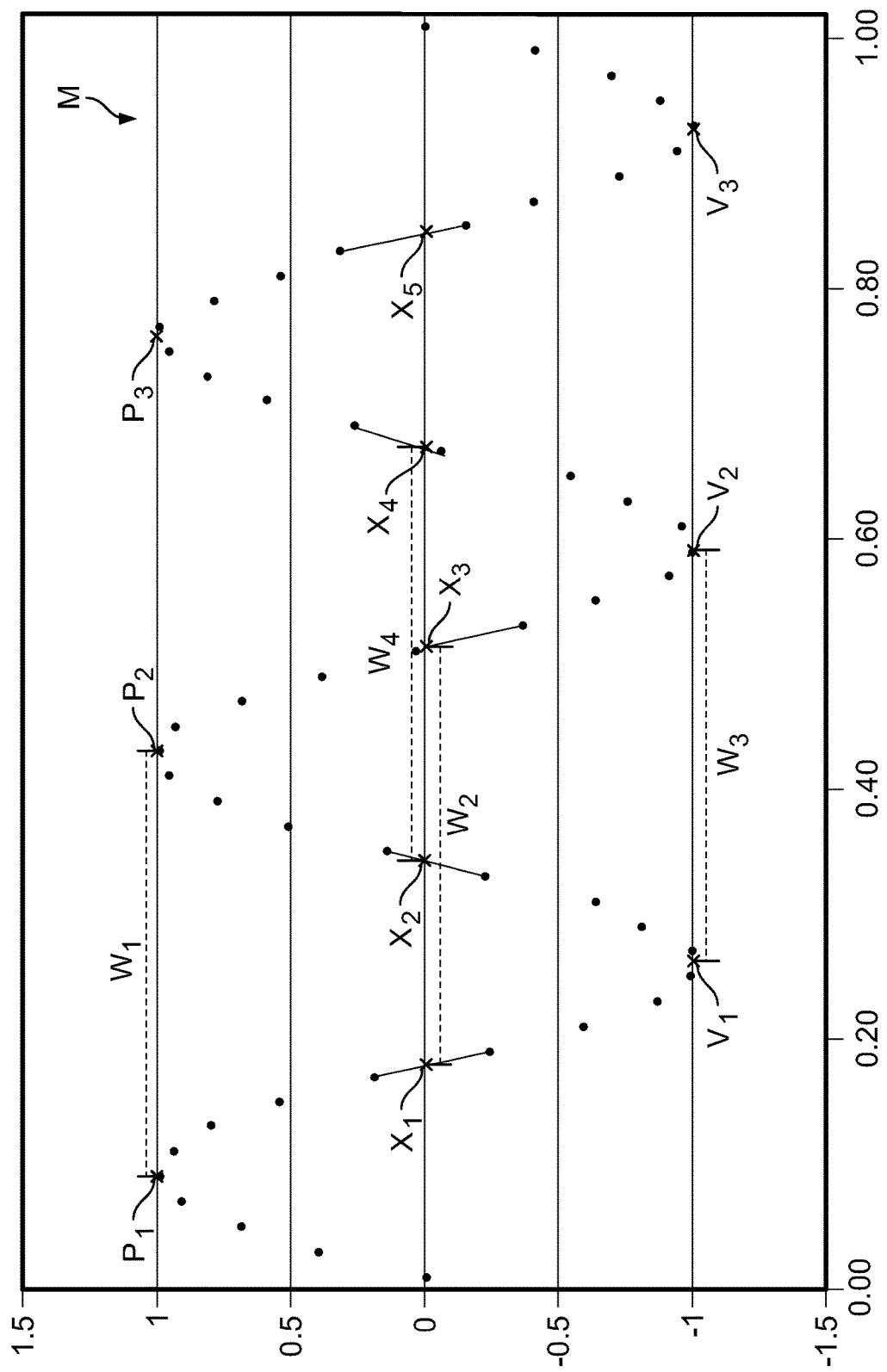
FIG. 8 shows the example series of filtered sample measurements of FIG. 7 with additional annotations to identify portions of the signal that are used in analyzing the periodicity of the repetitive motion.

At operation 326, the filtered signals are analyzed to determine the period of oscillation of the repetitive motion. FIGS. 7 and 8, which are discussed below, illustrate samples from an example signal and corresponding periods of repetitive motion. FIG. 7 shows an example series of filtered sample measurements M from an accelerometer captured over one second. FIG. 8 shows the same series of filtered sample measurements M with additional annotations to identify portions of the signal that are used in analyzing the periodicity of the repetitive motion. In some embodiments, each of the signals captured (i.e., the samples from each of the accelerometers in the accelerometer set) are analyzed to determine the period of oscillation of the repetitive motion. In other embodiments, a single signal is determined to be indicative of the cadence (see operation 328), and only this single signal is analyzed to determine the period of oscillation for the repetitive motion of that signal (operation 326). Therefore in some embodiments the operation 328 may be performed before operation 326.

In some embodiments, the period of repetitive motion is estimated by analyzing the filtered signals to identify (or approximate) zero crossings of the signal. In some embodiments, the zero crossings of the signal are approximated by linearly interpolating between two adjacent samples that are on opposite sides of zero. In FIG. 8, five example approximated zero crossings are shown as zero crossings $X_1$-$X_5$. Additionally, in some embodiments, minima and maxima are also identified (or approximated) for each oscillation. In some embodiments, a parabolic approximation is used to approximate the minima and maxima of each oscillation. Other embodiments may use the value of a local minimum or maximum sample point. In FIG. 6, the maxima (peaks) are shown as maxima $P_1$-$P_3$ and the minima (valleys) are shown as minima $V_1$-$V_3$.

In some embodiments, the period of the repetitive motion is then estimated by measuring the distance between equivalent points in adjacent oscillations. For example, in some embodiments, the period is estimated by calculating the distance between adjacent wave maxima (e.g., in FIG. 8, width $W_1$ between the maxima $P_1$ and the maxima $P_2$). Similarly, the period can be estimated by calculating the distance between adjacent falling zero crossings (e.g., in FIG. 8, width $W_2$ between the zero crossing $X_1$ and the zero crossing $X_3$) and between adjacent rising zero crossings (e.g., in FIG. 8, width $W_4$ between the zero crossing $X_2$ and the zero crossing $X_4$). Additionally, the period can be estimated by calculating the distance between adjacent wave minima (e.g., in FIG. 8, the width $W_3$ between minima $V_1$ and minima $V_2$). In this manner, the width of a period of a single oscillation is measured four times, with the measurements being offset from each other by quarter oscillations.

In some embodiments, during operation 326, a single measurement of the period of oscillation for each of the signals (e.g., from each of the accelerometers) is calculated and stored. In some embodiments, this single measurement is added to a First-In-First-Out buffer that operates as a circular buffer for storing a predetermined number of measurements. As operation 326 is repeated, the FIFO buffer fills up with measurements. When the FIFO buffer is full, new measurements replace the oldest measurement in the FIFO buffer. In this manner, the FIFO buffer operates to store a predetermined number of the most recent measurements of the period of oscillation. Some embodiments include multiple FIFO buffers and each of the multiple FIFO buffers is configured to store measurements determined from a different accelerometer. However, as noted above, in some embodiments, measurements are only determined for a single signal. In these embodiments, a single FIFO buffer may be used to store the measurements from the signal that has been identified as corresponding to cadence.

In at least some embodiments, one or more FIFO buffers are configured to each store twenty-four measurements. Because these width measurements are calculated at every quarter step, twenty-four measurements are captured across approximately six steps (which takes two seconds at an example running cadence of 180 steps per minute). Because the FIFO queues are updated based upon oscillations occurring in the filtered signals in some embodiments, if the user stops running and stands still, the FIFO buffer will not be updated (and beneficially the calculated cadence will not be impacted by the stop).

In some embodiments, the measurements stored in the FIFO buffer or buffers are converted to a log base 2 scale. Beneficially, when the measurements are converted to a log base 2 scale, the measurements remain linear across a range of cadence values.

At operation 328, a signal corresponding to the cadence is identified. In some embodiments, the signal corresponding to the cadence is a signal from at least one of the accelerometers that is most likely correlated with cadence. Because the orientation of the media-playback device 102 relative to the user U may not be fixed (e.g., when the media-playback device 102 is a smartphone or other mobile device), some embodiments analyze the signals captured by the various accelerometers to determine which of the accelerometers is oriented to detect movement in the direction of the repetitive motion at a given time. In other embodiments, a signal corresponding to the direction of relevant movement may be identified by combining the signals captured by multiple of the accelerometers.

In some embodiments, the signal corresponding to the direction of relevant movement is identified based on identifying the filtered accelerometer signal having the highest energy. In some embodiments, the energy of each of the filtered signals is calculated by rectifying the filtered signal and convoluting the rectified signal with a Hanning window of fifty samples (i.e., one second worth of samples at fifty Hz). Other embodiments use a number of samples selected from the range 10-100 samples. In some embodiments, other techniques are used to calculate the energy of the filtered signals.

In some embodiments, the highest energy signal is determined after each sample is recorded. In other embodiments, the highest energy signal is determined at a different interval. Further, in at least some embodiments, the identity of the highest energy signal is tracked (e.g., after every sample or every tenth sample) so that the identity of the highest-energy signal (and therefore the direction of the repetitive movement) can be updated if necessary. Beneficially, by tracking the highest energy signal, changes in the orientation of the media-playback device 102 will not interfere with identifying the accelerometer associated with the direction of the repetitive movement. In some embodiments, a signal corresponding to the cadence is identified by combining portions of multiple filtered series from different accelerometers to include the data from the series having the highest energy over each time interval.

In other embodiments, other methods of determining the direction of relative movement are used. For example, if the orientation of the media-playback device 102 relative to the user U is known or can be inferred, the signal from a particular accelerometer may be identified as corresponding to the expected direction of relevant motion based on the direction of movement to which the particular accelerometer is sensitive (which can be inferred from the orientation of the media-playback device 102 relative to the user). As an example, if the media-playback device 102 is oriented in an upright position, it can be inferred that that the Y accelerometer 276 will be sensitive to vertical movement such as would be expected from running. In this example, the signal from the Y accelerometer 276 is used in some embodiments.

At operation 330, a first aggregate value corresponding to the period of the oscillation over a first duration is calculated. In some embodiments, the first duration is based on a predetermined number of oscillations, such as six oscillations. Other embodiments have a first duration based on a different predetermined number of oscillations such as 4-10 oscillations. In other embodiments, the first duration corresponds to a predetermined time period such as 2-10 seconds.

In some embodiments, the first aggregate value is calculated by averaging multiple estimated widths of the period of oscillation. For example, in some embodiments, twenty-four estimated width values captured every quarter oscillation (e.g., the values stored in the FIFO buffer described at least with respect to operation 326) are averaged to generate the first aggregate value. In some embodiment, the FIFO buffer is updated with a new value every quarter oscillation and the first aggregate value is also recalculated every quarter oscillation using the updated values in the FIFO buffer. In some embodiments, the FIFO buffer is pre-populated with measurements that correspond to a typical cadence at the start of method 320 so that a reasonable first aggregate value may be calculated before enough measurements have been captured to fully fill the FIFO buffer. In some embodiments, the typical cadence value used to generate values to prepopulate the FIFO buffer is 165 steps per minute. In other embodiments, the typical cadence is calculated based on historic cadence information associated with the user (such as cadence data captured from previous similar activities performed by the user). Because the first aggregate value is based on averaging multiple measurements, in at least some embodiments, the aggregate value is not significantly affected by intermittent sampling errors or minor, short variations in cadence.

Furthermore, in some embodiments, a series of first aggregate values is generated as additional measurements are captured. In some embodiments, each of the values in the series of first aggregate values correspond to the period of oscillation at different time intervals over which the series of measurements span. In some embodiments, a first aggregate value is generated and included in the series after every quarter oscillation. In other embodiments, the first aggregate value is generated at a different frequency such as once every oscillation, once every second oscillation, etc.

At operation 332, a second aggregate value is calculated based on smoothing the first aggregate value. In some embodiments, the second aggregate value is updated (or re-calculated) when the first aggregate value is updated. In some embodiments, the second aggregate value is calculated using equation 1 shown below:

$$y(i)=y(i-1)+\alpha \times (x(i)-y(i-1)) \qquad (1)$$

where
  y(i) represents the currently calculated value for the second aggregate value;
  y(i−1) represents the previously calculated value for the second aggregate value;
  x(i) represents the most recently calculated value for the first aggregate value (e.g., as calculated by operation 330); and
  α is a smoothing coefficient.

In some embodiments, the smoothing coefficient α is 0.25. In other embodiments, the smoothing coefficient α is a value selected from the range 0.2-0.6. In yet other embodiments, the smoothing coefficient α is a value selected from the range 0.01-0.99. The smoothing coefficient α causes the second aggregate value to change more slowly than the first aggregate value changes in response to changes in cadence. In some embodiments, the second aggregate value is initially set to a value that corresponds to a cadence that is slightly lower than would be expected for the activity. For example, in some embodiments that relate to running, the second aggregate value is initially set to a value corresponding to a cadence of 140 steps per minute. In other embodiments, the second aggregate value is initially set to a value that is twenty-five steps per minute less than the user's historic average cadence for the activity.

In at least some embodiments, other equations or techniques are used to smooth the second aggregate value. Embodiments are possible using any technique for smoothing the second aggregate value in which a previously computed value for the second aggregate value is used in computing an updated value for the second aggregate value.

Like the first aggregate value, in some embodiments, a series of second aggregate values is generated as additional measurements are captured. In some embodiments, each of the values in the series of second aggregate values correspond to a smoothed first aggregate value for different time intervals over which the series of measurements span. Also like the series of first aggregate values, in various embodiments, the values in the series of second aggregate values are generated at various frequencies such as after every quarter oscillation, after every oscillation, after every other oscillation, etc.

At operation 334, it is determined whether the first aggregate value and the second aggregate value satisfy predetermined tolerances. As noted above, the second aggregate value changes more slowly than the first aggregate value changes in response to a change in cadence (e.g., when the user first starts running, when the runner changes cadence, etc.). Accordingly, in some embodiments, the difference between the first aggregate value and the second aggregate value indicates whether the user's cadence has been stable or changing recently.

In some embodiments, the predetermined tolerances include both a difference tolerance and a duration requirement. An example of a difference tolerance is predetermined number of steps per minute difference between the first aggregate value and the second aggregate value (e.g., within two steps per minute, or within a certain duration of time measured on a linear or log base 2 scale, etc.). An example of a duration requirement is a requirement that the first aggregate value and the second aggregate value satisfy the difference tolerance for a predetermined duration (e.g., the first aggregate value is within two steps per minute of the second aggregate value for at least two steps). In some embodiments, the predetermined duration is measured in steps, time, or otherwise.

If it is determined that the first aggregate value and the second aggregate value satisfy predetermined thresholds, the method 320 continues to operation 336 where the cadence is determined. If not, the method 320 continues to operation 338 where additional measurements are captured from the accelerometers in the accelerometer set and the process repeats starting at operation 324.

At operation 336, a cadence value is determined. In some embodiments, the cadence value is determined based on the second aggregate value. To determine a cadence value from the second aggregate value, the second aggregate value may need to be converted from a duration in log base 2 scale to a frequency value. Once the cadence value has been determined, it can be used for many purposes, including selecting appropriate media content items and determining an appropriate offset for phase aligning media content to cadence.

In some embodiments, the method 320 is used to both determine an initial cadence and to detect changes in cadence throughout an activity. As noted above, to detect an initial cadence, the FIFO buffer or buffers and second aggregate values may be set to certain initial values that are selected to minimize the number of steps (or time) required to accurately detect a stable cadence. For example, by populating the FIFO buffer or buffers with values that correspond to an expected (or typical) cadence value, the first aggregate value calculated by operation 330 will immediately be close to a value that corresponds to the user's instantaneous cadence. As another example, initially setting the second aggregate value to a value that corresponds to a cadence that is slightly outside of the expected range may prevent falsely determining a stable cadence before the user has actually reached a stable cadence. Instead, a stable cadence will be determined after the user has performed with a stable cadence for a sufficient time to cause the initially low second aggregate value to converge towards the first aggregate value. In some embodiments, a stable cadence is detected within ten to fifteen steps.

In some embodiments, a third aggregate value is calculated in a manner similar to the calculation of the second aggregate value (as described above with respect to operation 332). The third aggregate value may be used to determine when the user has changed cadence after an initial cadence has been determined. In some embodiments, the third aggregate value represents a smoothing of the second aggregate value. In this manner, the third aggregate value trails the second aggregate value and takes a longer time to react to changes in cadence. Additionally, in some embodiments, when the third aggregate value and the second aggregate value are within a predetermined difference threshold of each other for at least a predetermined duration threshold it is determined that the detected cadence value has stabilized. If the detected cadence value has stabilized at a value that is different from the previously determined cadence by a sufficient threshold a new cadence value is determined (and may be used in media content selection, phase alignment delay determination, or otherwise). Examples of sufficient thresholds include two steps per minute, five steps per minute, or ten steps per minute. In some embodiments, the sufficient threshold is a value selected from the range 1-15 steps per minute.

In at least some embodiments, the third aggregate value is calculated using an equation that is similar to equation 1 (described above with respect to operation 332) such as equation 2 shown below:

$$z(i)=z(i-1)+\beta \times (y(i)-z(i-1)) \qquad (2)$$

where
$z(i)$ represents the currently calculated value for the third aggregate value;
$z(i-1)$ represents the previously calculated value for the third aggregate value;
$y(i)$ represents the most recently calculated value for the second aggregate value (e.g., as calculated by operation 332); and
$\beta$ is a second smoothing coefficient.

The second smoothing coefficient $\beta$ is similar to the smoothing coefficient $\alpha$ and can be set to the same values and ranges described above. In some embodiments, the second smoothing coefficient $\beta$ is set to the same value as the smoothing coefficient $\alpha$, while in other embodiments the second smoothing coefficient $\beta$ is set to a different value than the smoothing coefficient $\alpha$. The second smoothing coefficient $\beta$ causes the third aggregate value to change even more slowly than the second aggregate value changes in response to changes in cadence. As mentioned above with respect to the second aggregate value, the third aggregate value is also calculated using other smoothing equations in some embodiments.

Like the first aggregate value and the second aggregate value, in some embodiments, a series of third aggregate values is generated. The values in the series of third aggregate values correspond to smoothed second aggregate values over various intervals over which the series of measurements span. The values in the series of third aggregate values may be generated at the same frequency as the values in the series of second aggregate values or at a different frequency.

Figure 9:
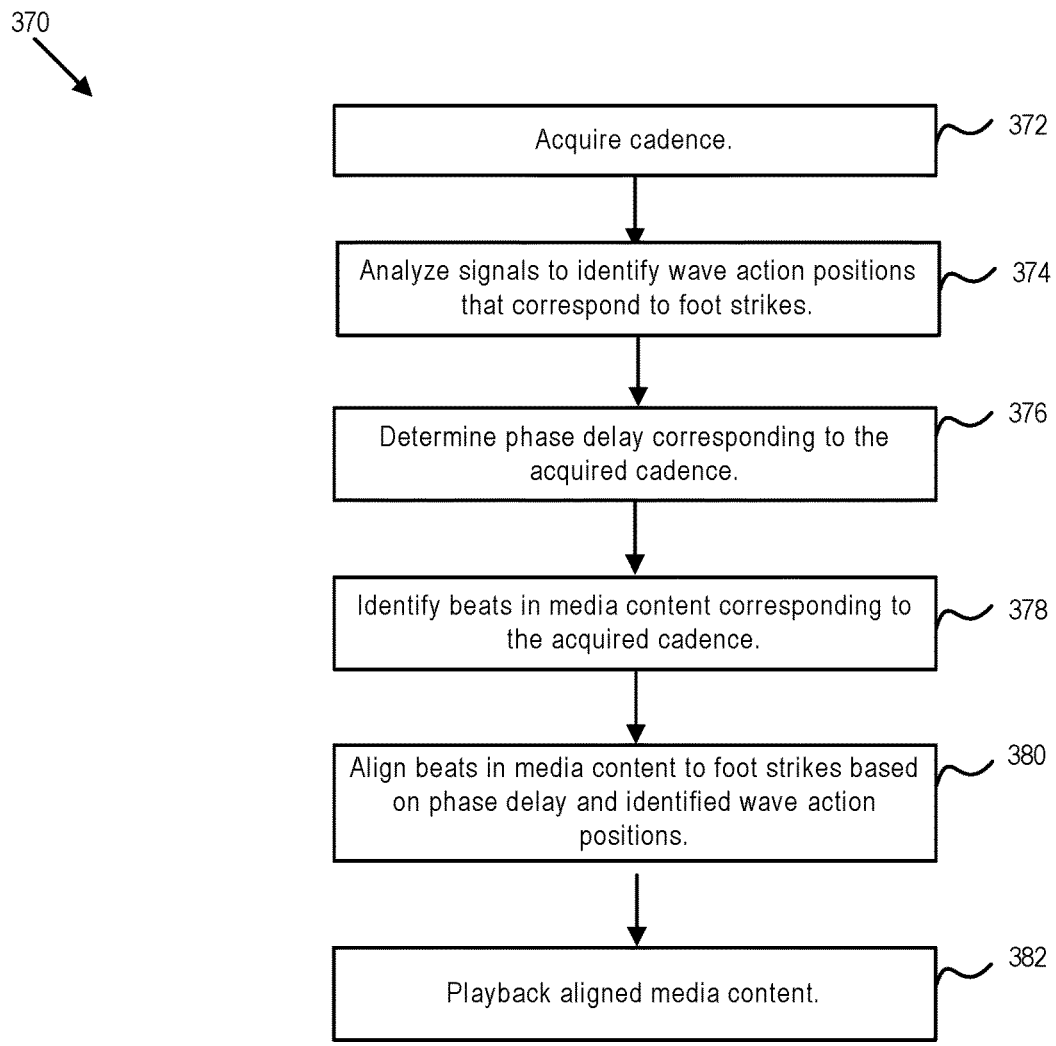
FIG. 9 illustrates an example method of phase aligning media content to cadence performed by some embodiments of the phase-aligned media playback engine of FIG. 3.

FIG. 9 illustrates an example method 370 of phase aligning media content to cadence performed by some embodiments of the phase-aligned media playback engine 242.

At operation 372, a cadence is acquired. The cadence may be acquired using the method 320 of determining cadence (described above with respect to at least FIGS. 6-8).

At operation 374, one or more signals are analyzed to identify wave action positions that correspond to foot strikes (or another type of action point in a repetitive-motion activity). In some embodiments, both a filtered signal and an unfiltered signal captured from at least one accelerometer are analyzed. In other embodiments, the signal that has been identified as corresponding to the cadence (e.g., as described above with respect to operation 328) is analyzed in conjunction with one or more corresponding unfiltered signals. Further, other embodiments analyze only a single signal, such as an unfiltered signal from an accelerometer, a filtered signal from an accelerometer, or the signal that has been identified as corresponding to the cadence.

Some embodiments operate to analyze the signals to detect the points at which acceleration towards the ground stops. Some example methods of detecting these points are described below.

In some orientations of the media-playback device 102, falling zero crossings in the filtered signal will approximately correspond to the foot strikes. Alternatively, in other orientations, the rising zero crossing in the acceleration signal 112 will approximately correspond to the foot strike. Example rising and falling zero crossings in an example acceleration signal are illustrated and described with respect to FIG. 8. In order to select between rising and falling zero crossings, some embodiments determine whether the positive direction of the acceleration signal is oriented towards or away from the ground. Because gravity exerts a constant force on the media-playback device 102 in the direction of ground, some embodiments analyze an unfiltered acceleration signal to identify whether the signal has more energy above the 0 axis or more energy below the 0 axis. The unfiltered signal is analyzed rather than the filtered signal because the filtered signal typically excludes the constant acceleration of gravity. If the unfiltered signal has more energy above the 0 axis, the positive direction of the acceleration signal is determined to be oriented towards the ground and consequently the falling zero crossings are determined to correspond to foot strikes; while if the signal has more energy above the 0 axis, the negative direction of the acceleration signal is determined to be oriented towards the ground and consequently the rising zero crossings are determined to correspond to foot strikes. In some embodiments, other metrics are used in addition to or instead of energy to determine which direction of the unfiltered acceleration signal is directed towards the ground. Additionally, the unfiltered signal may be filtered with a low-pass filter that operates to primarily preserve the constant portion (e.g., gravity) of the acceleration signal and then analyzed to determine the direction of the constant signal.

Additionally, some embodiments calculate or track an orientation of the media-playback device 102 to determine the wave action positions. Further, some embodiments communicate with external devices such as a sensor in a shoe that measures pressure or shock, which measurements are then used to determine the occurrence of foot strikes. In addition, some embodiments use a microphone to capture the sound of the user's footsteps to determine which portions of the waves correspond to the foot strikes.

Figure 10:
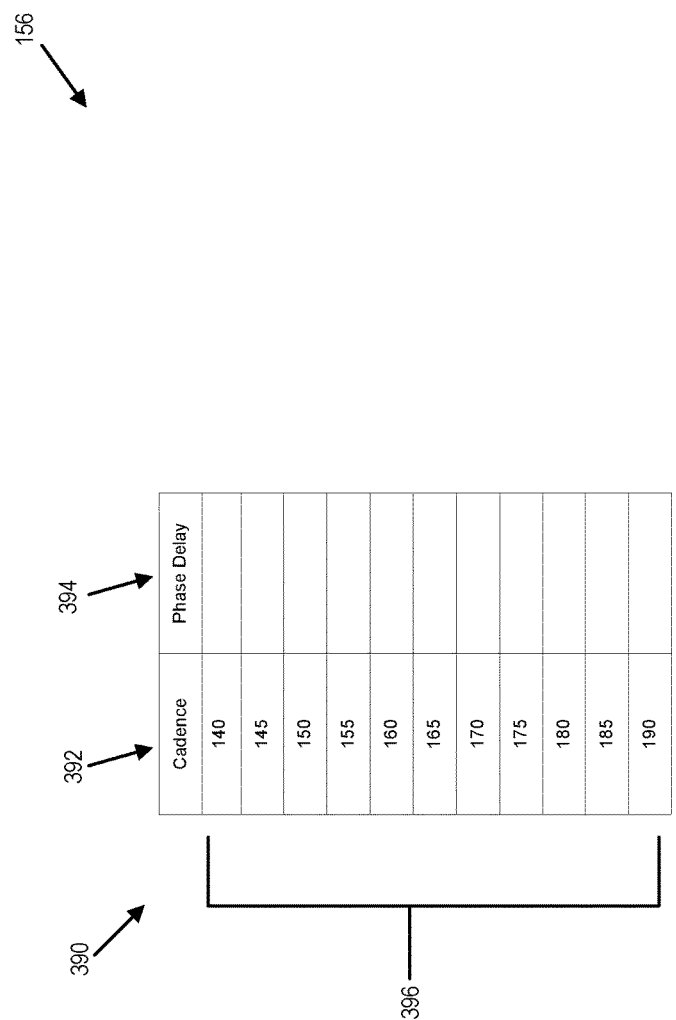
FIG. 10 illustrates an example cadence-phase delay data table that is stored in the memory device of FIG. 2 by some embodiments.

At operation 376, a phase delay corresponding to the acquired cadence is determined. In at least some embodiments, the phase delay is determined by accessing a table that relates phase delay values to cadence values. An example of such a table is shown in FIG. 10. In some embodiments, the phase delay value retrieved from the table is used directly. Additionally, in at least some embodiments, multiple phase delay values are retrieved and used to calculate a phase delay value corresponding to the acquired cadence. For example, if the acquired cadence is 177.5, some embodiments calculate the corresponding phase delay by interpolating between the phase delay value for a cadence of 175 and the phase delay value for a cadence of 180.

At operation 378, beats in media content corresponding to the acquired cadence are identified. In some embodiments, metadata accompanying a media content item includes annotations (or timestamps) that identify the temporal location of the beats. Additionally, some embodiments the annotations include an offset into the media content and a value corresponding to the interval between beats. In other embodiments, the media content item is processed to identify the location of the beats.

At operation 380, the beats in the media content are aligned to the foot strikes based on the phase delay value and the identified wave action positions. In some embodiments, the beats in the media content are aligned to the foot strikes by determining playback parameters for use playing back the media content. Examples of the playback parameters include a start time and an offset. Because the wave action positions (which correspond to, e.g., foot strikes) occur on a regular schedule the time of the next wave action position can be determined (or at least approximated) based on the period of oscillation (i.e., the inverse of the cadence) and the time of the last wave action position. In some embodiments, the predicted time of the next wave action position is identified as the time to start playback. In addition, some embodiments determine an offset into the media content item at which content playback should begin. In some embodiments, the offset is determined based on the identified location of the beats in the media content and the determined phase delay. For example, in some embodiments, offset into the content is determined by subtracting the phase delay from an identified beat location. In some embodiments, the remainder of the phase delay is divided by the period of oscillation is subtracted from an identified beat location to determine an offset instead.

The above is just one example technique to shift the media content playback to align it to a user's footsteps. There are many other ways of calculating the start time or offset values. Additionally, some embodiments do not use both a start time and an offset. For example, in some embodiments, playback begins immediately (i.e., the start time is the current time) and the offset value is adjusted accordingly. Similarly, rather than determining an offset, some embodiments adjust the start time to align the beat and the foot strikes.

At operation 382, playback of the media content item begins in accordance with the playback parameters determined in operation 380.

FIG. 10 illustrates an example cadence-phase delay data table 390 that is stored in the memory device 156 of some embodiments. The cadence-phase delay data table 390 stores values that represent the phase delay at particular cadence values. In some embodiments, the phase delay values represent the delay D, which combines multiple separate potential sources of delay and is discussed in greater detail with respect to at least FIG. 1. Furthermore, in at least some embodiments, the values stored in the cadence-phase delay data table 390 are calculated by the phase-delay calibration engine 244 and are used by the phase-aligned media playback engine 242. In some embodiments, the cadence-phase delay data table 390 is stored in the media-delivery system 104 instead of or in addition to being stored in the memory device 156. Additionally, some embodiments of the cadence-phase delay data table 390 are stored in a database or a file.

In the cadence-phase delay data table 390 the first column 392 stores a cadence value (such as a value selected from the range 140-190 steps per minute). The second column stores a phase delay value corresponding to the cadence value in the first column 392. In some embodiments, the cadence-phase delay data table 390 includes additional, fewer, or different columns.

Embodiments of the cadence-phase delay data table 390 can include any number of rows of data values. Some embodiments include a fixed set of cadence values and some embodiments include a dynamic set of cadence values. The example shown in FIG. 10 includes eleven rows with cadence values ranging from 140-190 steps per minute by increments of 5 steps per minute. Other embodiments include different numbers of rows spread across different ranges by different increments.

Additionally, some embodiments include multiple cadence-phase delay data tables. For example, some embodiments include one table for each user of the media-playback device 102 to account for differences in the phase delay between users (due at least differences in the physical delay). As another example, some embodiments include multiple tables corresponding to multiple profiles for a single user. The multiple profiles may relate to different carrying positions for the media-playback device 102 (e.g., one profile for when the media-playback device 102 is carried with an armband, one for when it is in a pocket, and another for when it is being carried in a hand). In some embodiments, the media-playback device 102 automatically determines which table to use. Additionally, in some embodiments, a user selects an appropriate table (or profile) for use in determining phase delay.

Figure 11:
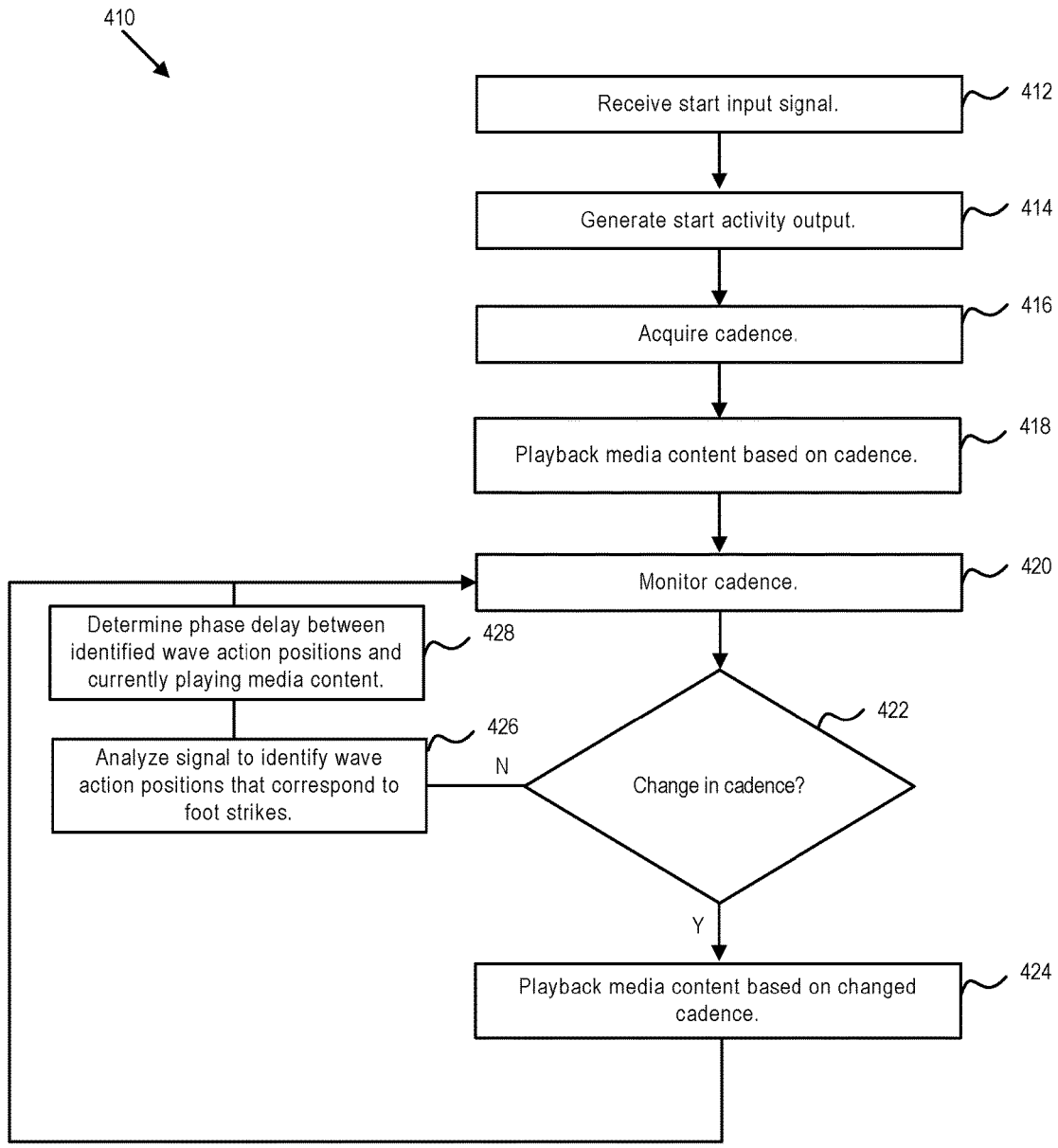
FIG. 11 illustrates an example method of calibrating the media-playback device of FIG. 1 for cadence and media content phase alignment performed by some embodiments of the phase-delay calibration engine of FIG. 3.

FIG. 11 illustrates an example method 410 of calibrating a media-playback device 102 for cadence and media content phase alignment performed by some embodiments of the phase-delay calibration engine 244. Such a method can be used, for example, the first time a user uses the media-playback device 102 while engage in a particular repetitive-motion activity to calibrate the device for the user and the activity. In some embodiments, the method is repeated on occasion to verify or adjust the calibration. Beneficially, processing cycles and power may be conserved by performing the method 410 initially and then occasionally rather than throughout the use of the device. However, some embodiments, perform the method 410 more frequently or even whenever the media playback device 102 is used while a user is engaged in a repetitive motion activity.

In at least some embodiments, the method 410 operates to determine one or more phase delay values for various cadences for a user. In some embodiments, the determined phase delay values are stored (e.g., in the cadence-phase delay data table 390 illustrated and described with respect to at least FIG. 10). Further, in some embodiments, the method 410 is performed automatically by the phase-delay calibration engine 244 while the media-playback device 102 is being used to playback content during a repetitive-motion activity. In at least some embodiments, the method 410 is performed transparently (i.e., without notice to or interference with the user) during media playback. Additionally, in some embodiments, performance of the method 410 is triggered by the user issuing a command to the media-playback device 102 (e.g., a voice command, menu or user interface selection, etc.).

At operation 412, a start input signal is received by the media-playback device 102. In at least some embodiments, the start input signal is received from a user and operates to indicate that the user desires to begin a calibration process. Additionally, in some embodiments, the start input signal operates to indicate that the user desires to start media playback to accompany a repetitive-motion activity. In some embodiments, the start input signal is similar to the start input signals of operation 252 (described at least with respect to FIG. 4). In fact, in some embodiments, the start input signal received in operation 412 is the same start input signal received in operation 252.

At operation 414, a start activity output is generated. In at least some embodiments, the start activity output operates to communicate to the user that the user should begin running (or a different repetitive-motion activity). In some embodiments, the start activity output is similar to the start activity output of operation 254 (described at least with respect for FIG. 4). In fact, in some embodiments, the start activity output generated in operation 414 is the same start activity output signal generated in operation 254. Additionally, in at least some embodiments, the start activity output directs the user to try to match his or her steps to the beat of the forthcoming media output.

At operation 416, a cadence associated with a repetitive-motion activity of the user is acquired. In some embodiments, the cadence is acquired by determining the cadence based on movements of the media-playback device 102 (e.g., using the methods illustrated and described with respect to at least FIGS. 5-8). In other embodiments, the cadence is acquired from a separate device, from a user input, or otherwise. Regardless of how the cadence is acquired, once the cadence is acquired, the method 410 continues to operation 418.

At operation 418, one or multiple media content items (e.g., a playlist) are identified for playback based on the acquired cadence and are played back by the media-playback device 102. In some embodiments, the media content items include music with a tempo that corresponds to the cadence. And the media content items that are played back can be stored locally in a file or streamed from an external source such as the media-delivery system 104. For example, in some embodiments, the media-playback device 102 requests media content items that correspond to the acquired cadence. Additionally, some embodiments generate a cadence acquired output upon determining the cadence (such as a sound or visual indicator).

In some embodiments, the identified media content is played back without any alignment. In this manner, the method 450 operates to determine appropriate phase delays when an appropriate phase delay is unknown. Alternatively, in some embodiments, a phase delay is determined based on the acquired cadence and the determined phase delay is applied to the identified media content to align the media content with the cadence. In this manner, the method 450 operates to verify or refine an existing phase delay value.

At operation 420, the cadence is monitored. In some embodiments, the cadence is monitored by continuing to detect the cadence associated with a repetitive movement of the media-playback device 102. In other embodiments, the cadence is monitored by continuing to acquire a cadence from a separate device, a user input, or otherwise.

At operation 422, it is determined whether the cadence has changed. In some embodiments, operation 422 determines whether the cadence has changed in a manner similar to operation 266 (described with respect to at least FIG. 4). If it is determined that a change in cadence has occurred the method 410 continues to operation 424, where media content based on the changed cadence is identified and played back. Additionally, in some embodiments, a cadence changed output is generated. Examples of cadence changed output are described with respect to at least operation 266 in FIG. 4.

In some embodiments, the media content items selected for playback based on the changed cadence are immediately played back after the change in cadence is detected (with or without crossfading). In other embodiments, the media-playback device 102 completes playback of the currently playing media content item before beginning to playback the newly selected media content items. Further, in some embodiments, the media-playback device 102 continues to playback the currently-playing media content item from a buffer until a second buffer can be sufficiently populated with stream data corresponding to the newly selected media content items. After operation 424, the method 410 returns to operation 420 where the cadence is monitored.

However, if instead it is determined that a change in cadence has not occurred at operation 422, the method continues to operation 426 where the phase delay is determined. In some embodiments, the method 410 does not continue to operation 426 until the runner has been running at the same cadence for at least a predetermined duration (e.g., time, number of steps, etc.) The predetermined duration may allow the runner to adjust his or her foot strikes to match the beat of the music included in the media content.

At operation 426, a signal is analyzed to identify wave action positions that correspond to foot strikes (or another type of action point in a repetitive-motion activity). In some embodiments, operation 426 identifies wave action positions in a manner similar to operation 374 (described with respect to at least FIG. 9).

As operation 428, a phase delay is determined for the current cadence. To determine the phase delay, the determined wave action positions are compared to the beats of the music included in the media content. In some embodiments, the temporal difference between a determined wave action position and a beat in the music is determined to be the phase delay. In some embodiments, the determined phase delay is calculated by averaging multiple measurements of the difference between a plurality of pairs of corresponding wave action positions and beats. This method for determining phase delay relies on the assumption that a typical user will adjust his or her foot strike to match the beat of the music. However, even if a particular does not adjust his or her foot strike to match the beat of the music, the described method will operate to determine a phase delay that will allow the media-playback device 102 to replicate the current relationship between beats and foot strikes (which may correspond to a preferred relationship for that user).

In some embodiments, the determined phase delay is stored (such as in cadence-phase delay data table 390, which is illustrated and described at least with respect to FIG. 10). Additionally, in some embodiments, the determined phase delay value is combined with previously determined values for phase delay that were captured at the same or a similar cadence. The multiple phase delay values may be combined into a single value using various techniques such as by calculating the mean, median, or mode of the multiple phase delay values. In some embodiments, other mathematical or statistical operations are used to determine a combined phase delay value from multiple measured phase delay values.

In at least some embodiments, after the phase delay value has been determined, the method 410 returns to operation 420 where the cadence continues to be monitored. In some embodiments, the phase delay determination described in operation 428 will be performed again after a sufficient period of time to confirm or adjust the phase delay value. Additionally, in some embodiments, the phase delay determination described in operation 428 is triggered when the runner changes to and stabilizes at a new cadence.

Figure 12:
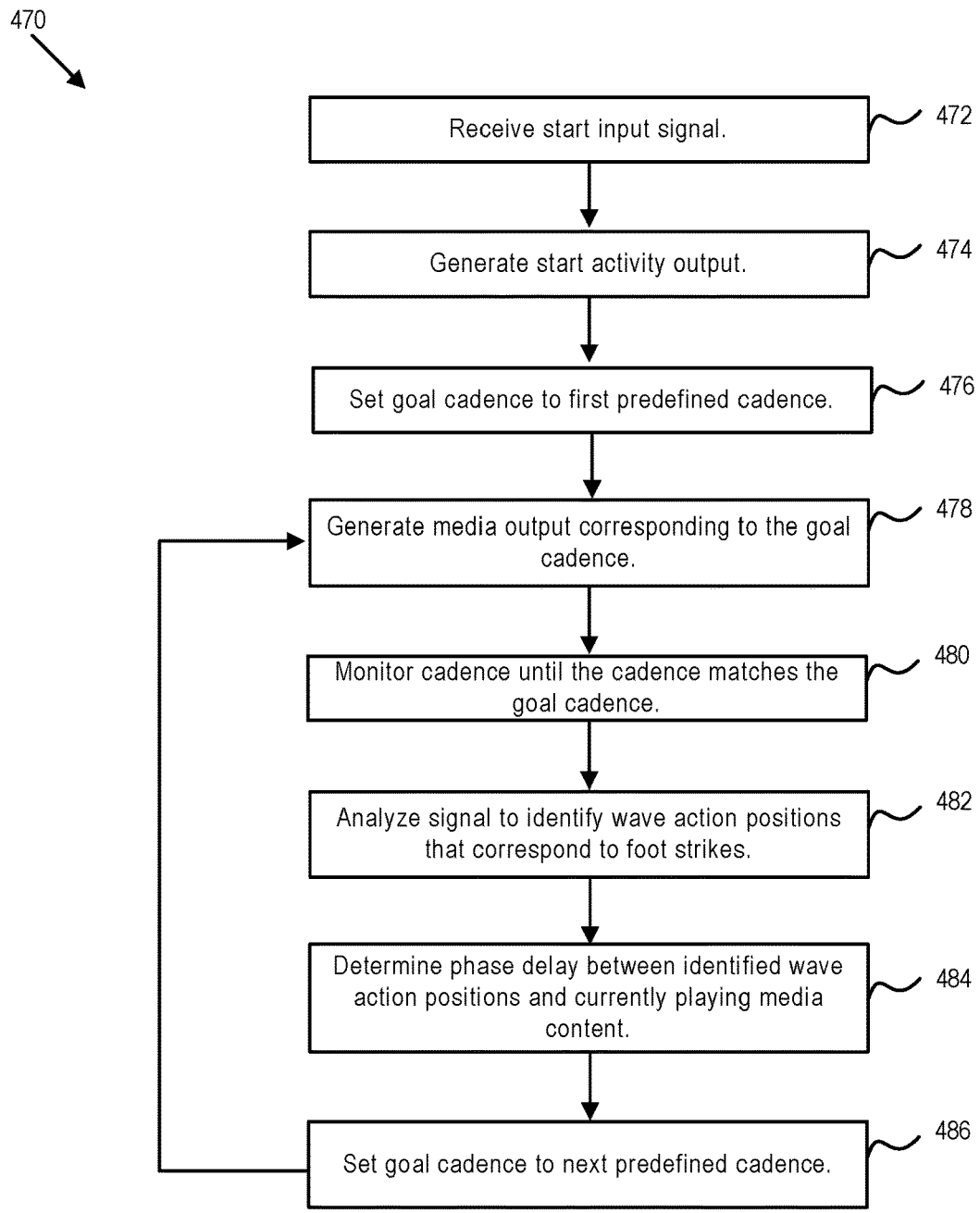
FIG. 12 illustrates another example method of calibrating the media-playback device of FIG. 1 for cadence and media content phase alignment performed by some embodiments of the phase-delay calibration engine of FIG. 3.

FIG. 12 illustrates another example method 470 of calibrating a media-playback device 102 for cadence and media content phase alignment performed by some embodiments of the phase-delay calibration engine 244. In at least some embodiments, the method 470 operates to guide a user through a calibration process for a list of predetermined cadences to generate phase delay values for each of the cadences. In some embodiments, these phase delay values are stored in the cadence-phase delay data table 390 (illustrated and described at least with respect to FIG. 10). In some embodiments, the predetermined cadences in the list are selected by a user. In other embodiments, the predetermined cadences are automatically determined to span a range of typical cadences for a particular repetitive-motion activity. For example, an example list of predetermined cadences for running includes cadence values between 140-190 steps per minute at increments of five steps per minute.

At operation 472, a start input signal is received by the media-playback device 102. In at least some embodiments, the start input signal is received from a user and operates to indicate that the user desires to begin a calibration process. In some embodiments, the start input signal is similar to the start input signals of operation 252 (described at least with respect to FIG. 4).

At operation 474, a start activity output is generated. In at least some embodiments, the start activity output operates to communicate to the user that the user should begin running (or another repetitive-motion activity). In some embodiments, the start activity output is similar to the start activity output of operation 254 (described at least with respect for FIG. 4). Additionally, in at least some embodiments, the start activity output directs the user to try to match the beat of the forthcoming media output.

At operation 476, a goal cadence is set to the first cadence in the list of predetermined cadences. Additionally, in some embodiments, a goal cadence output is generated to alert the user of the goal cadence. For example, some embodiments playback a voice over that states the goal cadence. Additionally, some embodiments, generate visual indicators of the goal cadence.

At operation 478, media output corresponding to the goal cadence is generated. In some embodiments, a media content item having a tempo equal to or approximately equal to the goal cadence is identified and played back. Additionally, in at least some embodiments, rather than playing back a media content item, an audible output (such as a metronome-like sound) is generated at a tempo corresponding to the goal cadence.

At operation 480, the cadence associated with a repetitive-motion activity of the user is acquired and monitored until the cadence matches the goal cadence. In some embodiments, the cadence is acquired by determining the cadence based on movements of the media-playback device 102 (e.g., using the methods illustrated and described with respect to at least FIGS. 5-8). In other embodiments, the cadence is acquired from a separate device, from a user input, or otherwise. Regardless of how the cadence is acquired, once that cadence is acquired, the method 470 continues to operation 482. In some embodiments, the cadence is monitored indefinitely. In other embodiments, the cadence is monitored for a predetermined time period and if the goal cadence is not reached within that time period, the method 470 continues to operation 486 where the goal cadence is set to the next predefined cadence.

At operation 482, a signal is analyzed to identify wave action positions that correspond to foot strikes (or another type of action point in a repetitive-motion activity). In some embodiments, operation 482 identifies wave action positions in a manner similar to operation 374 (described with respect to at least FIG. 9).

As operation 484, a phase delay is determined for the goal cadence. Example methods of determining the phase delay are described with respect to operation 428 (described at least with respect to FIG. 11). Similar to the phase delay determined in operation 428, the phase delay is stored or combined with other phase delay measurements for later use.

At operation 486, the goal cadence is set to the next predefined cadence in the list. In some embodiments, if the phase delay has been determined for all of the predefined cadences in the list, the method 470 ends. Additionally, in some embodiments, the determined phase delay values are evaluated and compared to one another to detect outlier values. A phase delay value may be determined to be an outlier if it is significantly different from the other phase delay values. Additionally, in some embodiments a phase delay value is determined to be an outlier if it is sufficiently different (e.g., the magnitude of difference is greater than a predetermined threshold) from a value predicted based on other phase delay values (such as by extrapolating from neighboring phase delay values or curve fitting other phase delay values).

The method 470 may be performed multiple times for the same user to generate phase delay values for different physical configurations of the media-playback device 102 (e.g., for the different ways the media-playback device 102 may be held during the repetitive-motion activity or for different repetitive motion activities, etc.).

Figure 13:
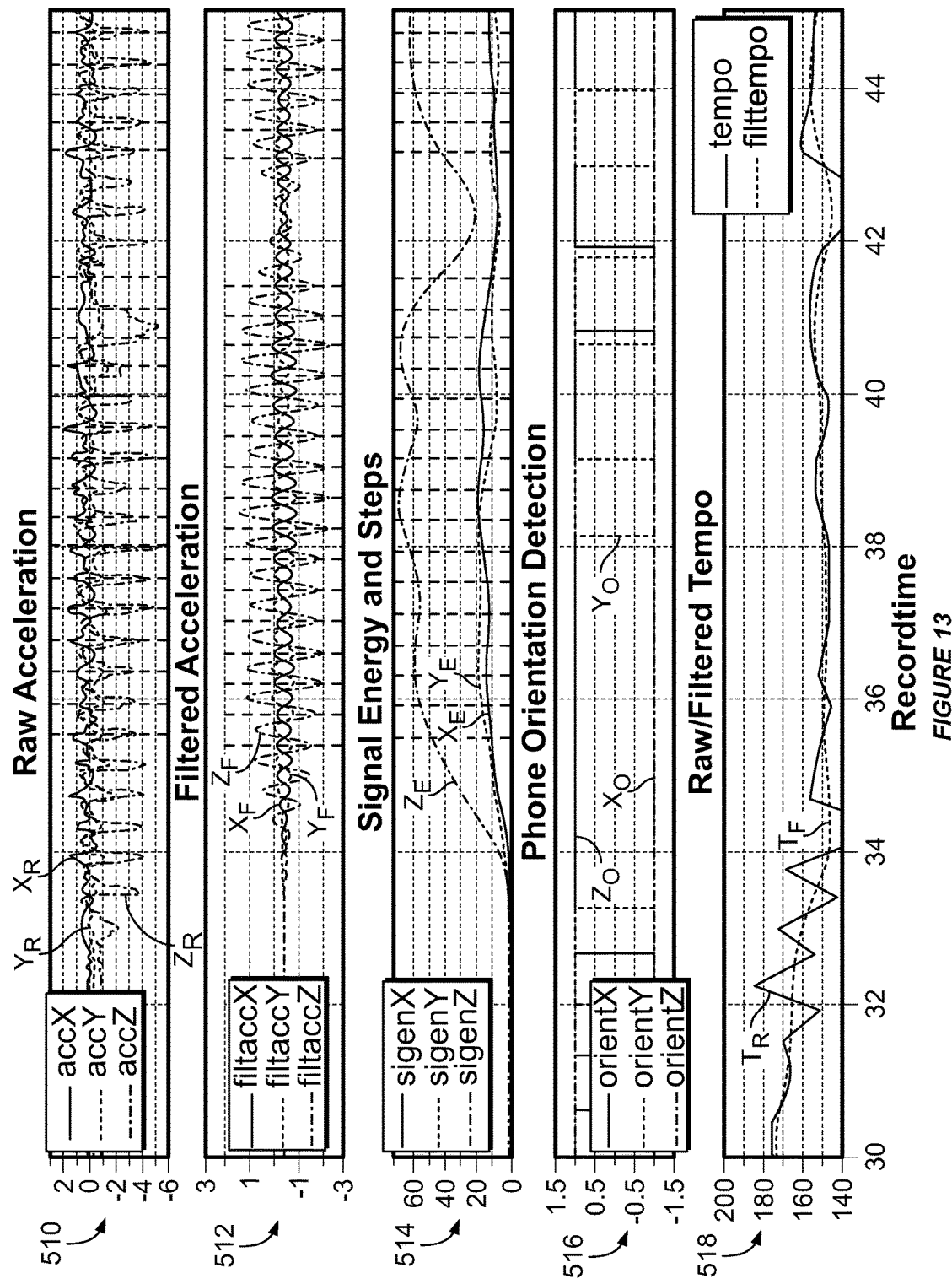
FIG. 13 shows example sequences of measurements that are captured and produced by some embodiments of the media-playback device of FIG. 1.

FIG. 13 shows example sequences of measurements that are captured and produced by some embodiments of the media-playback device 102. This example includes a raw acceleration data panel 510, a filtered acceleration data panel 512, an signal energy panel 514, an orientation panel 516, and a tempo panel 518.

The raw acceleration data panel 510 illustrates sequences of sample acceleration data $X_R$, $Y_R$, and $Z_R$, captured by some embodiments of the X accelerometer 274, Y accelerometer 276, and Z accelerometer 278 respectively. The sequences shown in this panel have not been filtered with a band-pass filter.

The filtered acceleration data panel 512 includes sequences of sample filtered acceleration data $X_F$, $Y_F$, and $Z_F$, corresponding to the acceleration data illustrated in the raw acceleration data panel 510.

The signal energy panel 514 includes sequences of signal energy values $X_E$, $Y_E$, and $Z_E$, corresponding to the filtered acceleration data illustrated in the filtered acceleration data panel 512.

The orientation panel 516 includes sequences of orientation values $X_O$, $Y_O$, and $Z_O$, determined by analyzing the corresponding raw acceleration data illustrated in the raw acceleration data panel 510.

The tempo panel 518 includes a sequence of raw tempo values $T_R$ and a sequence of filtered tempo values $T_F$ calculated based on the acceleration data captured and illustrated in raw acceleration data panel 510 and at least some of the various other signals illustrated herein.

As noted previously, although many of the examples provided above are described with respect to running, other embodiments relate to other repetitive motion activities as well such as cycling, swimming, and rowing.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A media-playback device for aligning play back of media content for a user performing a running activity, the media-playback device comprising:
   a content output device that operates to output media content;
   a cadence-acquiring device comprising a movement-determining device and a cadence-determination engine configured to determine a cadence based on movement data captured by the movement-determining device;
   a phase-delay calibration engine configured to determine phase delay values for at least one cadence value, wherein the phase-delay calibration engine determines the phase delay values based at least in part on a time required to detect a foot strike within the running activity;
   a cadence-based media content selection engine configured to identify a media content item based on the cadence determined by the cadence-acquiring device, wherein the media content item comprises music with a tempo that corresponds to the cadence; and
   a phase-aligned media playback engine configured to:
      align the identified media content item to the running activity using at least one of the determined phase-delay values; and
      cause the media-output device to output the aligned media content item so that a beat of the media content item is output coincidentally with an expected foot strike.

2. The media-playback device of claim 1, wherein the phase-aligned media playback engine is further configured to:
   identify foot strikes within the running activity based on the movement data.

3. The media-playback device of claim 1, wherein the phase-aligned media playback engine is further configured to:
   identify a wave action position within an oscillation of a filtered sequence of measurements captured by the measurement-determining device corresponding to the foot strike based on calculating an orientation of the media-playback device.

4. The media-playback device of claim 1, wherein the phase-aligned media playback engine is further configured to:
   determine a phase delay value corresponding to the determined cadence; and
   align the identified media content item to the running activity based on the determined phase delay.

5. The media-playback device of claim 1, wherein the cadence-based media content selection engine is configured to identify a media content item that includes music with a tempo that is within a predetermined threshold of the cadence.

6. The media-playback device of claim 1, wherein the cadence-based media content selection engine is further configured to:
   monitor for changes in cadence; and
   upon detecting a change in cadence:
      identify a second media content item based on a changed cadence;
      align the second media content item to the running activity; and
      cause the media-output device to playback the aligned second media content item.

7. The media-playback device of claim 1, wherein the measurement-determining device comprises three orthogonally-oriented accelerometers and the cadence-determination engine is configured to:
   capture a sequence of measurements from each of the three accelerometers;
   filter the sequences of measurements based on frequency to generate filtered sequences;

identify the sequence of measurements corresponding to cadence, wherein the sequence is identified based on calculating energy values for each of the sequences.

8. The media-playback device of claim 1, wherein the media playback engine is configured to identify wave action positions corresponding to foot strikes.

9. The media-playback device of claim 1, wherein measurements are captured at a sample rate in the range of 20-200 Hz.

10. The media-playback device of claim 1, wherein the media content item is stored locally on the media-playback device.

11. The media-playback device of claim 1, wherein the media content item is streamed to the media-playback device by a media-delivery system based on a request for media content items that specifies the cadence.

12. The media-playback device of claim 1, wherein the media-playback device is a smartphone.

13. A method of cadence-based media playback for use during repetitive-motion activities comprising:
determining a cadence associated with a repetitive-motion activity based on acceleration data captured by a plurality of accelerometers, wherein the acceleration data comprises sequences of acceleration sample data captured from each of the plurality of accelerometers over a duration of time, the repetitive-motion activity including a repetitive cycle of motion having a repetitive action point;
identifying a media content item based on the determined cadence;
phase aligning the identified media content item to the repetitive-motion activity using a phase delay value, wherein the phase delay value is determined based at least in part on a time required to detect the repetitive action point within the repetitive-motion activity; and
playing back the aligned media content item so that a beat of the media content item is output coincidentally with an expected repetitive action point.

14. The method of claim 13 further comprising:
filtering the sequences of measurements based on frequency to generate filtered sequences;
identifying a cadence signal corresponding to the cadence of the repetitive-motion activity from the filtered sequences; and
analyzing the cadence signal to identify a wave action position corresponding to the repetitive action point within the repetitive-motion activity.

15. The method of claim 14, wherein analyzing the cadence signal comprises:
identifying a portion of the cadence signal corresponding to an oscillation of the repetitive-motion activity;
determining an orientation of the cadence signal relative to the ground; and
selecting a point within the oscillation that corresponds to the acceleration towards the ground stopping as the wave action position.

16. The method of claim 13, further comprising:
determining a phase delay value corresponding to the determined cadence; and
aligning the identified media content item to the repetitive-motion activity using the determined phase delay.

17. A method of calibrating a cadence-based media playback device for use during repetitive-motion activities comprising:
generating media output, wherein the media output has a tempo;
determining a cadence associated with a repetitive-motion activity based on acceleration data captured by a plurality of accelerometers, wherein the acceleration data comprises sequences of acceleration sample data captured from each of the plurality of accelerometers over a duration of time, the repetitive-motion activity including a repetitive cycle of motion having a repetitive action point;
determining whether the tempo of the media output corresponds to the determined cadence; and
upon determining that the tempo of the media output corresponds to the determined cadence, calculating a phase delay value for the determined cadence based on the repetitive action point within the repetitive-motion activity and a beat within the media output, wherein the phase delay is determined based at least in part on a time required to detect the repetitive action point within the repetitive-motion activity, and wherein the phase delay indicates a shift in playback of the media output that is needed so that a beat of the media output is output coincidentally with an expected repetitive action point.

18. The method of claim 17, wherein the tempo of the media output is selected to correspond to a goal cadence selected from a predefined list of cadence values.

19. The method of claim 13, wherein the repetitive-motion activity includes a running activity.

20. The method of claim 13, further comprising storing the phase delay value for use in phase aligning media content to a repetitive-motion activity for play back during the repetitive-motion activity.

* * * * *